(12) United States Patent
Feldman

(10) Patent No.: US 9,950,043 B2
(45) Date of Patent: Apr. 24, 2018

(54) MODULATION OF MUSCLE AND ADIPOCYTE DISTRIBUTION AND FATE

(71) Applicant: The Board of Trustees of the Leland Stanford Junior University, Stanford, CA (US)

(72) Inventor: Brian Jay Feldman, Berkeley, CA (US)

(73) Assignee: The Board of Trustees of the Leland Stanford Junior University, Stanford, CA (US)

(*) Notice: Subject to any disclaimer, the term of this patent is extended or adjusted under 35 U.S.C. 154(b) by 0 days. days.

(21) Appl. No.: 14/442,704

(22) PCT Filed: Nov. 15, 2013

(86) PCT No.: PCT/US2013/070389
§ 371 (c)(1),
(2) Date: May 13, 2015

(87) PCT Pub. No.: WO2014/078713
PCT Pub. Date: May 22, 2014

(65) Prior Publication Data
US 2016/0287682 A1    Oct. 6, 2016

Related U.S. Application Data

(60) Provisional application No. 61/726,932, filed on Nov. 15, 2012.

(51) Int. Cl.
| | | |
|---|---|---|
| A61K 38/48 | (2006.01) | |
| A61K 35/34 | (2015.01) | |
| C12N 5/077 | (2010.01) | |
| C12N 9/64 | (2006.01) | |

(52) U.S. Cl.
CPC .......... *A61K 38/4886* (2013.01); *A61K 35/34* (2013.01); *C12N 5/0659* (2013.01); *C12N 9/6494* (2013.01); *C12N 2501/734* (2013.01); *C12Y 304/24* (2013.01)

(58) Field of Classification Search
CPC .. A61K 38/4886; A61K 35/34; C12N 5/0659; C12N 2501/734; C12Y 304/24
See application file for complete search history.

(56) References Cited

U.S. PATENT DOCUMENTS

| | | | |
|---|---|---|---|
| 2002/0077465 A1 | 6/2002 | Shi et al. | |
| 2003/0022352 A1* | 1/2003 | Hirose | A23L 33/17 435/226 |
| 2004/0258669 A1* | 12/2004 | Dzau | C12N 5/0663 424/93.21 |
| 2010/0184033 A1 | 7/2010 | West et al. | |
| 2011/0236953 A1 | 9/2011 | Walsh et al. | |

FOREIGN PATENT DOCUMENTS

WO    WO 97/40072    10/1997

OTHER PUBLICATIONS

Boonen et al. The Muscle Stem Cell Niche: Regulation of Satellite Cells During Regeneration. Tissue Engineering Part B, v14(4), p. 419-431.*
Vazquez et al. Meth-1, a Human Ortholog of ADAMTS-1, and METH-2 are Members of a New Family of Proteins with Angio-inhibitory Activity. The Journal of Biological Chemistry (1999), v274(33), p. 23349-23357.*
Cornelison et al. Context Matters: In Vivo and In Vitro Influences on Muscle Satellite Cell Activity. Journal of Cellular Biochemistry (2008), v105, p. 663-669.*
Park et al. Mammalian Target of Rapamycin (mTOR) Signaling Is Required for a Late-stage Fusion Process during Skeletal Myotube Maturation. The Journal of Biological Chemistry (2005), v280(36), p. 32009-32017. (Year: 2005).*
Rodriguez-Manzaneque, Juan Carlos et al., Characterization of METH-1/ADAMTS1 Processing Reveals Two Distinct Active Forms, the Journal of Biological Chemistry, Aug. 15, 2000, vol. 275, No. 43; pp. 33471-33479.
Stankusas, Kryn et al., Endocardial Brg1 Represses ADAMTS1 to Maintain the Microenvironment for Myocardial Morphogenesis, Dev Cell. Feb. 12, 2008, vol. 14, No. 2, pp. 298-311.

* cited by examiner

*Primary Examiner* — Sean C. Barron
(74) *Attorney, Agent, or Firm* — Pamela J. Sherwood; Bozicevic, Field & Francis LLP

(57) ABSTRACT

Modulation of the ADAMTS1 signaling pathway alters the commitment of progenitor cells to a muscle fate; and increases muscle mass.

7 Claims, 16 Drawing Sheets
(9 of 16 Drawing Sheet(s) Filed in Color)

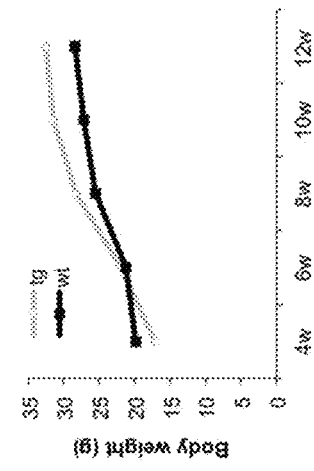
FIGURE 9A
FIGURE 9B
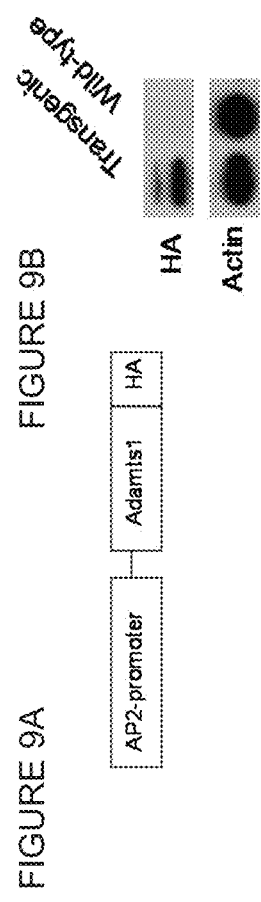
FIGURE 9C
FIGURE 9D
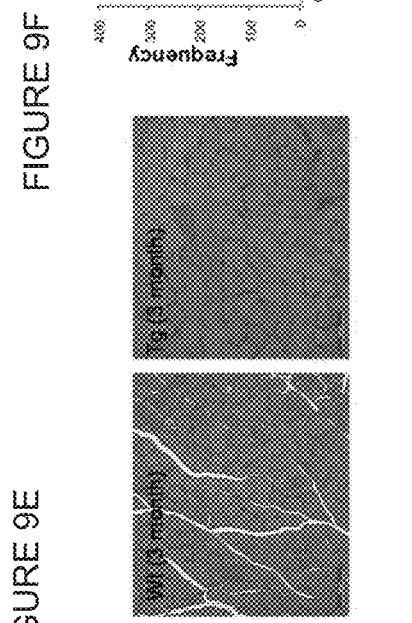
FIGURE 9E
FIGURE 9F
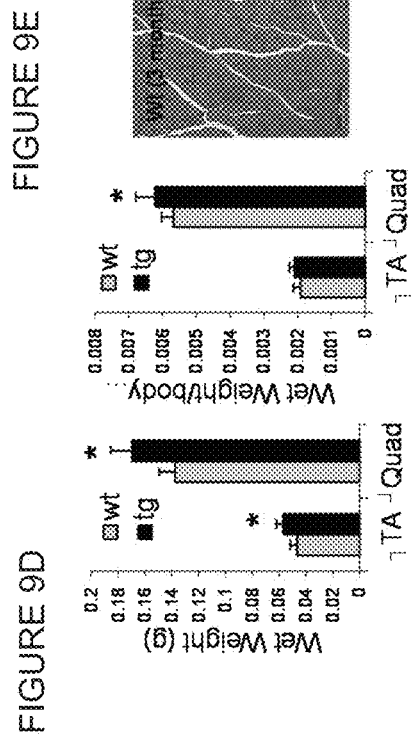

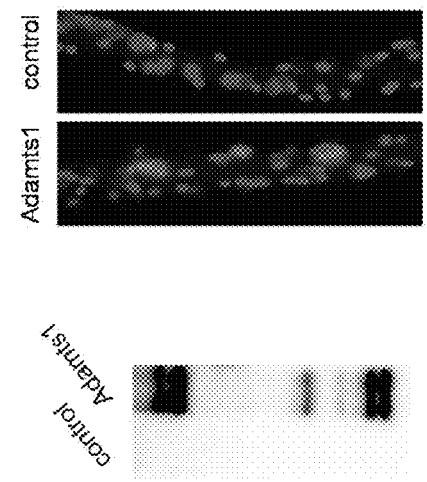
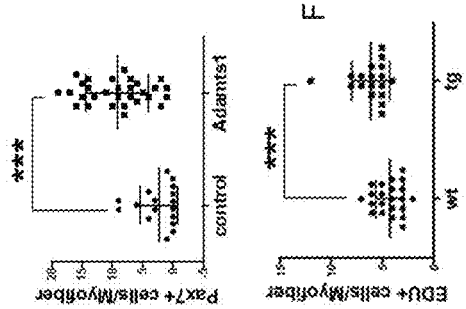
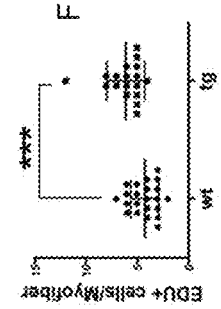
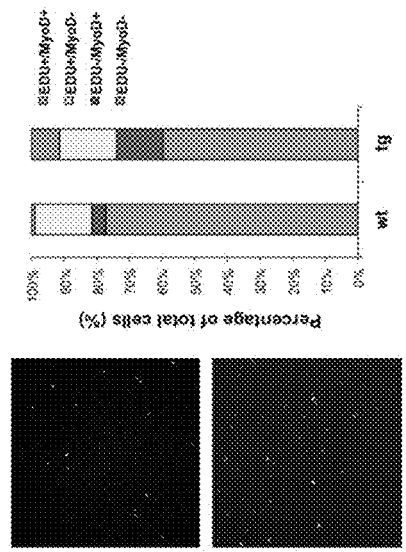
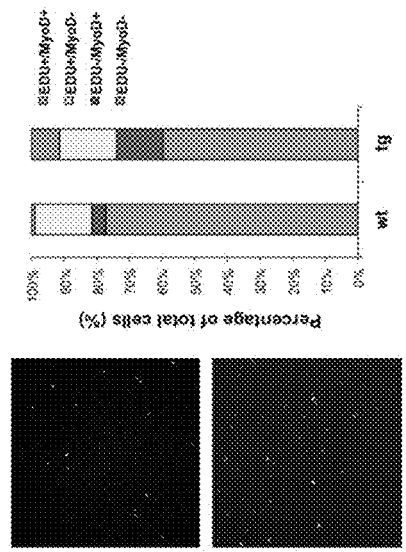
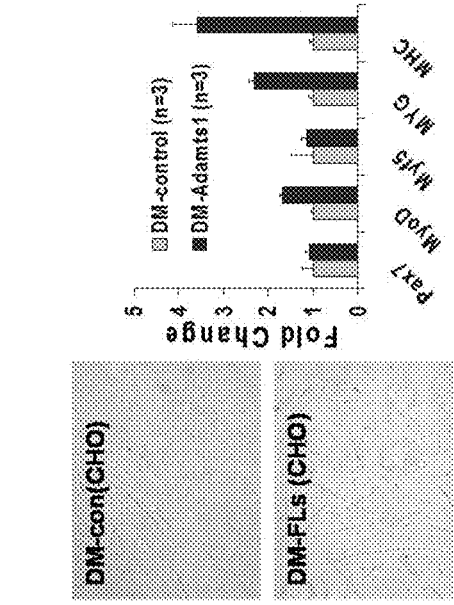
FIGURE 10A
FIGURE 10B
FIGURE 10C
FIGURE 10D
FIGURE 10E
FIGURE 10F

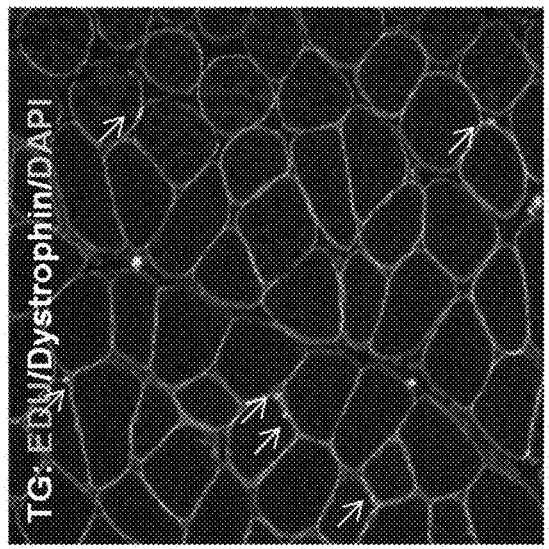
FIGURE 11A  FIGURE 11B
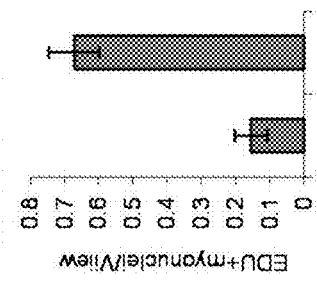
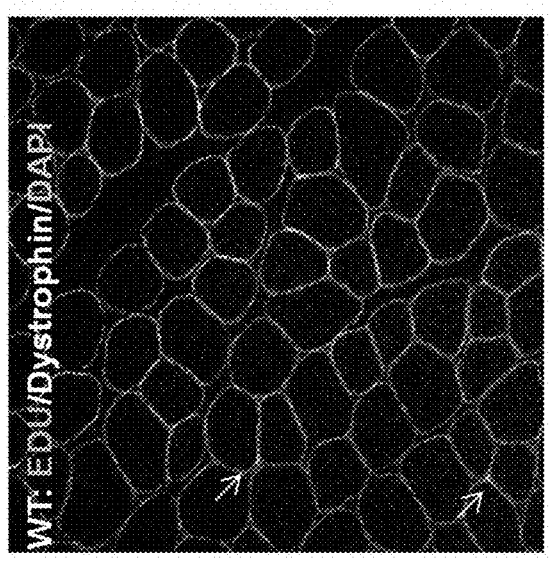
FIGURE 11C
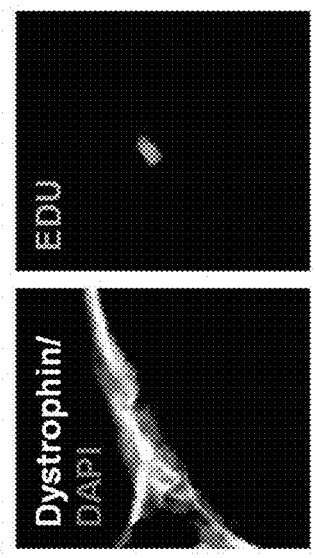
FIGURE 11D

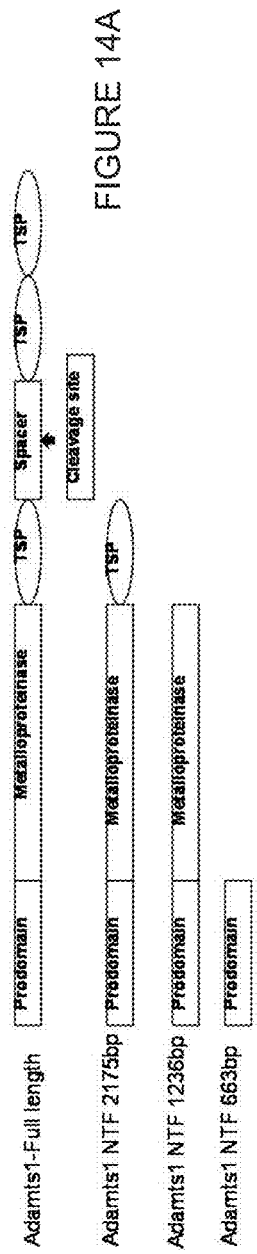
FIGURE 14A
FIGURE 14B
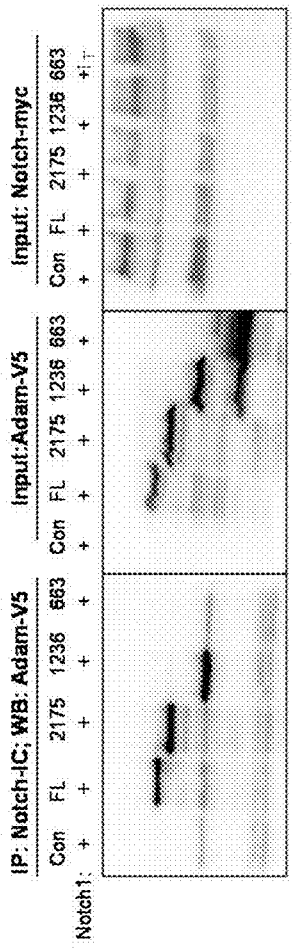
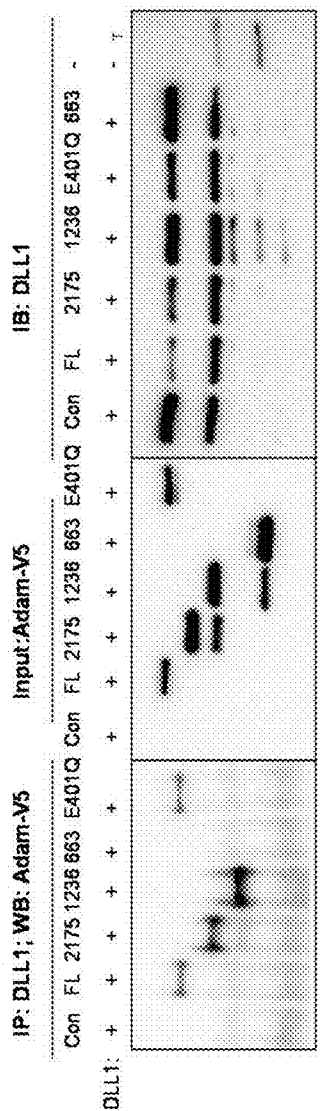
FIGURE 14C

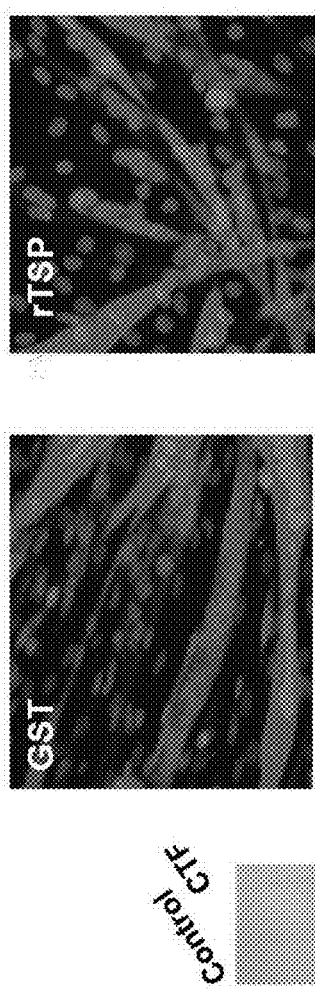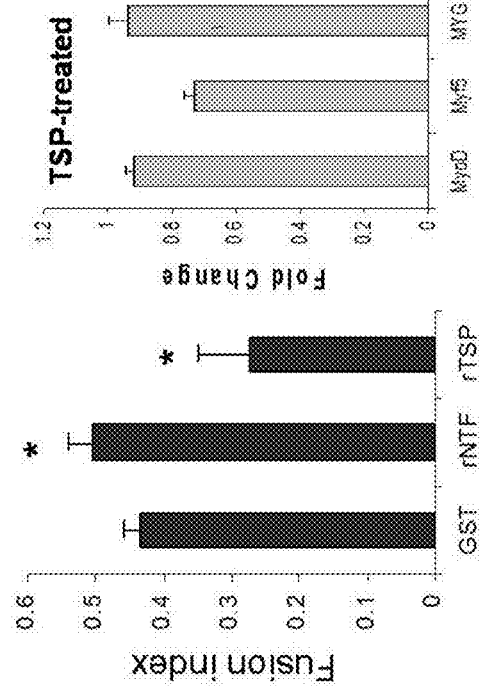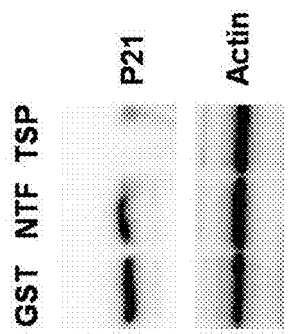
FIGURE 15A
FIGURE 15B
FIGURE 15C
FIGURE 15D
FIGURE 15E

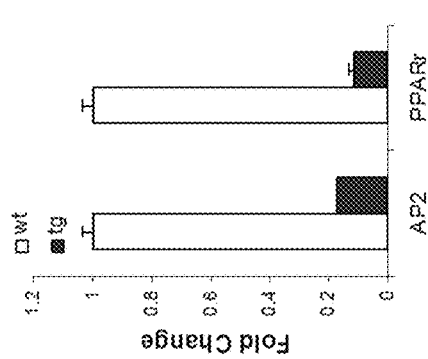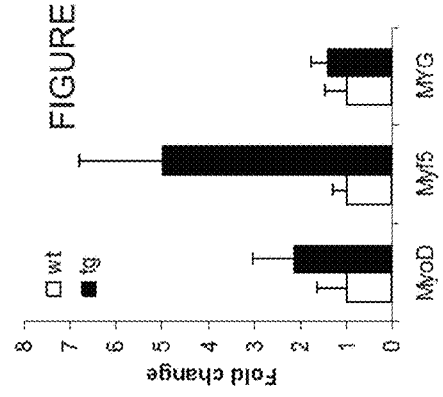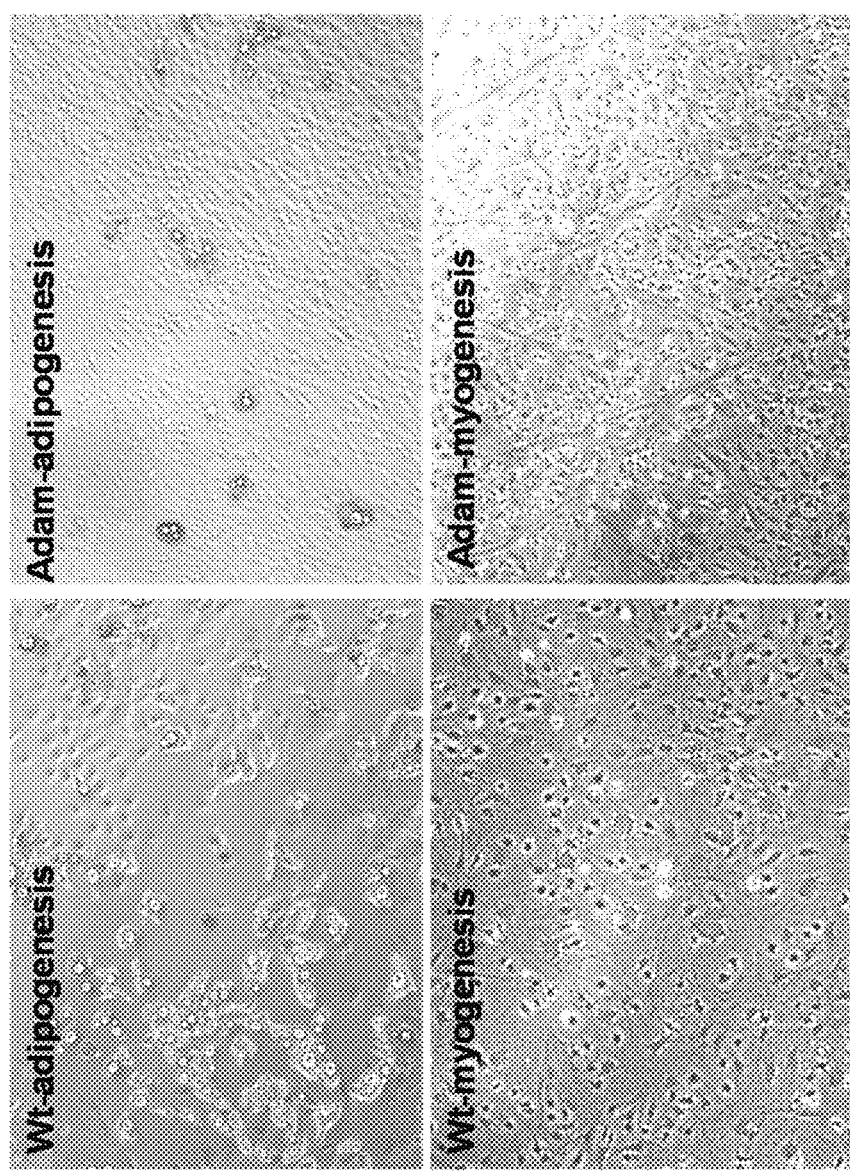

SEQUENCE LISTING

```
<160> NUMBER OF SEQ ID NOS: 7

<210> SEQ ID NO 1
<211> LENGTH: 967
<212> TYPE: PRT
<213> ORGANISM: Homo sapiens

<400> SEQUENCE: 1

Met Gln Arg Ala Val Pro Glu Gly Phe Gly Arg Arg Lys Leu Gly Ser
1               5                   10                  15

Asp Met Gly Asn Ala Glu Arg Ala Pro Gly Ser Arg Ser Phe Gly Pro
            20                  25                  30

Val Pro Thr Leu Leu Leu Leu Ala Ala Ala Leu Leu Ala Val Ser Asp
        35                  40                  45

Ala Leu Gly Arg Pro Ser Glu Glu Asp Glu Glu Leu Val Val Pro Glu
    50                  55                  60

Leu Glu Arg Ala Pro Gly His Gly Thr Thr Arg Leu Arg Leu His Ala
65                  70                  75                  80

Phe Asp Gln Gln Leu Asp Leu Glu Leu Arg Pro Asp Ser Ser Phe Leu
                85                  90                  95

Ala Pro Gly Phe Thr Leu Gln Asn Val Gly Arg Lys Ser Gly Ser Glu
            100                 105                 110
```

```
Thr Pro Leu Pro Glu Thr Asp Leu Ala His Cys Phe Tyr Ser Gly Thr
    115                 120                 125

Val Asn Gly Asp Pro Ser Ser Ala Ala Leu Ser Leu Cys Glu Gly
    130                 135                 140

Val Arg Gly Ala Phe Tyr Leu Leu Gly Glu Ala Tyr Phe Ile Gln Pro
145                 150                 155                 160

Leu Pro Ala Ala Ser Glu Arg Leu Ala Thr Ala Ala Pro Gly Glu Lys
                165                 170                 175

Pro Pro Ala Pro Leu Gln Phe His Leu Leu Arg Arg Asn Arg Gln Gly
            180                 185                 190

Asp Val Gly Gly Thr Cys Gly Val Val Asp Glu Pro Arg Pro Thr
            195                 200                 205

Gly Lys Ala Glu Thr Glu Asp Glu Asp Glu Gly Thr Glu Gly Glu Asp
    210                 215                 220

Glu Gly Ala Gln Trp Ser Pro Gln Asp Pro Ala Leu Gln Gly Val Gly
225                 230                 235                 240

Gln Pro Thr Gly Thr Gly Ser Ile Arg Lys Lys Arg Phe Val Ser Ser
                245                 250                 255

His Arg Tyr Val Glu Thr Met Leu Val Ala Asp Gln Ser Met Ala Glu
            260                 265                 270

Phe His Gly Ser Gly Leu Lys His Tyr Leu Leu Thr Leu Phe Ser Val
            275                 280                 285

Ala Ala Arg Leu Tyr Lys His Pro Ser Ile Arg Asn Ser Val Ser Leu
    290                 295                 300

Val Val Val Lys Ile Leu Val Ile His Asp Glu Gln Lys Gly Pro Glu
305                 310                 315                 320

Val Thr Ser Asn Ala Ala Leu Thr Leu Arg Asn Phe Cys Asn Trp Gln
                325                 330                 335

Lys Gln His Asn Pro Pro Ser Asp Arg Asp Ala Glu His Tyr Asp Thr
            340                 345                 350

Ala Ile Leu Phe Thr Arg Gln Asp Leu Cys Gly Ser Gln Thr Cys Asp
    355                 360                 365

Thr Leu Gly Met Ala Asp Val Gly Thr Val Cys Asp Pro Ser Arg Ser
    370                 375                 380

Cys Ser Val Ile Glu Asp Asp Gly Leu Gln Ala Ala Phe Thr Thr Ala
385                 390                 395                 400

His Glu Leu Gly His Val Phe Asn Met Pro His Asp Asp Ala Lys Gln
                405                 410                 415

Cys Ala Ser Leu Asn Gly Val Asn Gln Asp Ser His Met Met Ala Ser
            420                 425                 430

Met Leu Ser Asn Leu Asp His Ser Gln Pro Trp Ser Pro Cys Ser Ala
    435                 440                 445

Tyr Met Ile Thr Ser Phe Leu Asp Asn Gly His Gly Glu Cys Leu Met
    450                 455                 460

Asp Lys Pro Gln Asn Pro Ile Gln Leu Pro Gly Asp Leu Pro Gly Thr
465                 470                 475                 480

Ser Tyr Asp Ala Asn Arg Gln Cys Gln Phe Thr Phe Gly Glu Asp Ser
                485                 490                 495

Lys His Cys Pro Asp Ala Ala Ser Thr Cys Ser Thr Leu Trp Cys Thr
            500                 505                 510

Gly Thr Ser Gly Gly Val Leu Val Cys Gln Thr Lys His Phe Pro Trp
    515                 520                 525
```

-continued

Ala Asp Gly Thr Ser Cys Gly Glu Gly Lys Trp Cys Ile Asn Gly Lys
530                 535                 540

Cys Val Asn Lys Thr Asp Arg Lys His Phe Asp Thr Pro Phe His Gly
545                 550                 555                 560

Ser Trp Gly Met Trp Gly Pro Trp Gly Asp Cys Ser Arg Thr Cys Gly
        565                 570                 575

Gly Gly Val Gln Tyr Thr Met Arg Glu Cys Asp Asn Pro Val Pro Lys
            580                 585                 590

Asn Gly Gly Lys Tyr Cys Glu Gly Lys Arg Val Arg Tyr Arg Ser Cys
        595                 600                 605

Asn Leu Glu Asp Cys Pro Asp Asn Asn Gly Lys Thr Phe Arg Glu Glu
610                 615                 620

Gln Cys Glu Ala His Asn Glu Phe Ser Lys Ala Ser Phe Gly Ser Gly
625                 630                 635                 640

Pro Ala Val Glu Trp Ile Pro Lys Tyr Ala Gly Val Ser Pro Lys Asp
            645                 650                 655

Arg Cys Lys Leu Ile Cys Gln Ala Lys Gly Ile Gly Tyr Phe Phe Val
        660                 665                 670

Leu Gln Pro Lys Val Val Asp Gly Thr Pro Cys Ser Pro Asp Ser Thr
    675                 680                 685

Ser Val Cys Val Gln Gly Gln Cys Val Lys Ala Gly Cys Asp Arg Ile
690                 695                 700

Ile Asp Ser Lys Lys Lys Phe Asp Lys Cys Gly Val Cys Gly Gly Asn
705                 710                 715                 720

Gly Ser Thr Cys Lys Lys Ile Ser Gly Ser Val Thr Ser Ala Lys Pro
            725                 730                 735

Gly Tyr His Asp Ile Ile Thr Ile Pro Thr Gly Ala Thr Asn Ile Glu
        740                 745                 750

Val Lys Gln Arg Asn Gln Arg Gly Ser Arg Asn Asn Gly Ser Phe Leu
    755                 760                 765

Ala Ile Lys Ala Ala Asp Gly Thr Tyr Ile Leu Asn Gly Asp Tyr Thr
770                 775                 780

Leu Ser Thr Leu Glu Gln Asp Ile Met Tyr Lys Gly Val Val Leu Arg
785                 790                 795                 800

Tyr Ser Gly Ser Ser Ala Ala Leu Glu Arg Ile Arg Ser Phe Ser Pro
            805                 810                 815

Leu Lys Glu Pro Leu Thr Ile Gln Val Leu Thr Val Gly Asn Ala Leu
        820                 825                 830

Arg Pro Lys Ile Lys Tyr Thr Tyr Phe Val Lys Lys Lys Glu Ser
    835                 840                 845

Phe Asn Ala Ile Pro Thr Phe Ser Ala Trp Val Ile Glu Glu Trp Gly
850                 855                 860

Glu Cys Ser Lys Ser Cys Glu Leu Gly Trp Gln Arg Arg Leu Val Glu
865                 870                 875                 880

Cys Arg Asp Ile Asn Gly Gln Pro Ala Ser Glu Cys Ala Lys Glu Val
            885                 890                 895

Lys Pro Ala Ser Thr Arg Pro Cys Ala Asp His Pro Cys Pro Gln Trp
        900                 905                 910

Gln Leu Gly Glu Trp Ser Ser Cys Ser Lys Thr Cys Gly Lys Gly Tyr
    915                 920                 925

Lys Lys Arg Ser Leu Lys Cys Leu Ser His Asp Gly Gly Val Leu Ser
930                 935                 940

His Glu Ser Cys Asp Pro Leu Lys Lys Pro Lys His Phe Ile Asp Phe

```
                945                 950                 955                 960
Cys Thr Met Ala Glu Cys Ser
                    965

<210> SEQ ID NO 2
<211> LENGTH: 847
<212> TYPE: PRT
<213> ORGANISM: Mus musculus

<400> SEQUENCE: 2

Met Gln Pro Lys Val Pro Leu Gly Ser Arg Lys Gln Lys Pro Cys Ser
1               5                   10                  15

Asp Met Gly Asp Val Gln Arg Ala Ala Arg Ser Arg Gly Ser Leu Ser
            20                  25                  30

Ala His Met Leu Leu Leu Leu Ala Ser Ile Thr Met Leu Leu Cys
        35                  40                  45

Ala Arg Gly Ala His Gly Arg Pro Thr Glu Glu Asp Glu Glu Leu Val
    50                  55                  60

Leu Pro Ser Leu Glu Arg Ala Pro Gly His Asp Ser Thr Thr Thr Arg
65              70                  75                  80

Leu Arg Leu Asp Ala Phe Gly Gln Gln Leu His Leu Lys Leu Gln Pro
                85                  90                  95

Asp Ser Gly Phe Leu Ala Pro Gly Phe Thr Leu Gln Thr Val Gly Arg
            100                 105                 110

Ser Pro Gly Ser Glu Ala Gln His Leu Asp Pro Thr Gly Asp Leu Ala
        115                 120                 125

His Cys Phe Tyr Ser Gly Thr Val Asn Gly Asp Pro Gly Ser Ala Ala
    130                 135                 140

Ala Leu Ser Leu Cys Glu Gly Val Arg Gly Ala Phe Tyr Leu Gln Gly
145             150                 155                 160

Glu Glu Phe Phe Ile Gln Pro Ala Pro Gly Val Ala Thr Glu Arg Leu
                165                 170                 175

Ala Pro Ala Val Pro Glu Glu Glu Ser Ser Ala Arg Pro Gln Phe His
            180                 185                 190

Ile Leu Arg Arg Arg Arg Gly Ser Gly Gly Ala Lys Cys Gly Val
        195                 200                 205

Met Asp Asp Glu Thr Leu Pro Thr Ser Asp Ser Arg Pro Glu Ser Gln
    210                 215                 220

Asn Thr Arg Asn Gln Trp Pro Val Arg Asp Pro Thr Pro Gln Asp Ala
225             230                 235                 240

Gly Lys Pro Ser Gly Pro Gly Ser Ile Arg Lys Lys Arg Phe Val Ser
                245                 250                 255

Ser Pro Arg Tyr Val Glu Thr Met Leu Val Ala Asp Gln Ser Met Ala
            260                 265                 270

Asp Phe His Gly Ser Gly Leu Lys His Tyr Leu Leu Thr Leu Phe Ser
        275                 280                 285

Val Ala Ala Arg Phe Tyr Lys His Pro Ser Ile Arg Asn Ser Ile Ser
    290                 295                 300

Leu Val Val Val Lys Ile Leu Val Ile Tyr Glu Glu Lys Gly Pro
305             310                 315                 320

Glu Val Thr Ser Asn Ala Ala Leu Thr Leu Arg Asn Phe Cys Asn Trp
                325                 330                 335

Gln Lys Gln His Asn Ser Pro Ser Asp Arg Asp Pro Gly His Tyr Asp
            340                 345                 350
```

```
Thr Ala Ile Leu Phe Thr Arg Gln Asp Leu Cys Gly Ser His Thr Cys
        355                 360                 365

Asp Thr Leu Gly Met Ala Asp Val Gly Thr Val Cys Asp Pro Ser Arg
    370                 375                 380

Ser Cys Ser Val Ile Glu Asp Gly Leu Gln Ala Ala Phe Thr Thr
385                 390                 395                 400

Ala His Glu Leu Gly His Val Phe Asn Met Pro His Asp Asp Ala Lys
                405                 410                 415

His Cys Ala Ser Leu Asn Gly Val Thr Gly Asp Ser His Leu Met Ala
            420                 425                 430

Ser Met Leu Ser Ser Leu Asp His Ser Gln Pro Trp Ser Pro Cys Ser
        435                 440                 445

Ala Tyr Met Val Thr Ser Phe Leu Asp Asn Gly His Gly Glu Cys Leu
    450                 455                 460

Met Asp Lys Pro Gln Asn Pro Ile Lys Leu Pro Ser Asp Leu Pro Gly
465                 470                 475                 480

Thr Leu Tyr Asp Ala Asn Arg Gln Cys Gln Phe Thr Phe Gly Glu Glu
                485                 490                 495

Ser Lys His Cys Pro Asp Ala Ala Ser Thr Cys Thr Thr Leu Trp Cys
            500                 505                 510

Thr Gly Thr Ser Gly Gly Leu Leu Val Cys Gln Thr Lys His Phe Pro
        515                 520                 525

Trp Ala Asp Gly Thr Ser Cys Gly Glu Gly Lys Trp Cys Val Ser Gly
    530                 535                 540

Lys Cys Val Asn Lys Thr Asp Met Lys His Phe Ala Thr Pro Val His
545                 550                 555                 560

Gly Ser Trp Gly Pro Trp Gly Pro Trp Gly Asp Cys Ser Arg Thr Cys
                565                 570                 575

Gly Gly Gly Val Gln Tyr Thr Met Arg Glu Cys Asp Asn Pro Val Pro
            580                 585                 590

Lys Asn Gly Gly Lys Tyr Cys Glu Gly Lys Arg Val Arg Tyr Arg Ser
        595                 600                 605

Cys Asn Ile Glu Asp Cys Pro Asp Asn Asn Gly Lys Thr Phe Arg Glu
    610                 615                 620

Glu Gln Cys Glu Ala His Asn Glu Phe Ser Lys Ala Ser Phe Gly Asn
625                 630                 635                 640

Glu Pro Thr Val Glu Trp Thr Pro Lys Tyr Ala Gly Val Ser Pro Lys
                645                 650                 655

Asp Arg Cys Lys Leu Thr Cys Glu Ala Lys Gly Ile Gly Tyr Phe Phe
            660                 665                 670

Val Leu Gln Pro Lys Val Val Asp Gly Thr Pro Cys Ser Pro Asp Ser
        675                 680                 685

Thr Ser Val Cys Val Gln Gly Gln Cys Val Lys Ala Gly Cys Asp Arg
    690                 695                 700

Ile Ile Asp Ser Lys Lys Phe Asp Lys Cys Gly Val Cys Gly Gly
705                 710                 715                 720

Asn Gly Ser Thr Cys Lys Lys Met Ser Gly Ile Val Thr Ser Thr Arg
                725                 730                 735

Pro Gly Tyr His Asp Ile Val Thr Ile Pro Ala Gly Ala Thr Asn Ile
            740                 745                 750

Glu Val Lys His Arg Asn Gln Arg Gly Ser Arg Asn Asn Gly Ser Phe
        755                 760                 765

Leu Ala Ile Arg Ala Ala Asp Gly Thr Tyr Ile Leu Asn Gly Asn Phe
```

```
            770                 775                 780
Thr Leu Ser Thr Leu Glu Gln Asp Leu Thr Tyr Lys Gly Thr Val Leu
785                 790                 795                 800

Arg Tyr Ser Gly Ser Ser Ala Ala Leu Glu Arg Ile Arg Ser Phe Ser
                805                 810                 815

Pro Leu Lys Glu Pro Leu Thr Ile Gln Val Leu Met Val Gly His Ala
                820                 825                 830

Leu Arg Pro Lys Ile Lys Phe Thr Tyr Phe Lys Lys Lys Lys
                835                 840                 845

<210> SEQ ID NO 3
<211> LENGTH: 607
<212> TYPE: PRT
<213> ORGANISM: Artificial sequence
<220> FEATURE:
<223> OTHER INFORMATION: Synthetic amino acid sequence

<400> SEQUENCE: 3

Ala Leu Leu Ala Val Ser Asp Ala Leu Gly Arg Pro Ser Glu Glu Asp
1               5                   10                  15

Glu Glu Leu Val Val Pro Glu Leu Glu Arg Ala Pro Gly His Gly Thr
                20                  25                  30

Thr Arg Leu Arg Leu His Ala Phe Asp Gln Gln Leu Asp Leu Glu Leu
            35                  40                  45

Arg Pro Asp Ser Ser Phe Leu Ala Pro Gly Phe Thr Leu Gln Asn Val
    50                  55                  60

Gly Arg Lys Ser Gly Ser Glu Thr Pro Leu Pro Glu Thr Asp Leu Ala
65                  70                  75                  80

His Cys Phe Tyr Ser Gly Thr Val Asn Gly Asp Pro Ser Ser Ala Ala
                85                  90                  95

Ala Leu Ser Leu Cys Glu Gly Val Arg Gly Ala Phe Tyr Leu Leu Gly
                100                 105                 110

Glu Ala Tyr Phe Ile Gln Pro Leu Pro Ala Ala Ser Glu Arg Leu Ala
            115                 120                 125

Thr Ala Ala Pro Gly Glu Lys Pro Pro Ala Pro Leu Gln Phe His Leu
    130                 135                 140

Leu Arg Arg Asn Arg Gln Gly Asp Val Gly Gly Thr Cys Gly Val Val
145                 150                 155                 160

Asp Asp Glu Pro Arg Pro Thr Gly Lys Ala Glu Thr Glu Asp Glu Asp
                165                 170                 175

Glu Gly Thr Glu Gly Glu Asp Glu Gly Ala Gln Trp Ser Pro Gln Asp
                180                 185                 190

Pro Ala Leu Gln Gly Val Gly Gln Pro Thr Gly Thr Gly Ser Ile Arg
            195                 200                 205

Lys Lys Arg Phe Val Ser Ser His Arg Tyr Val Glu Thr Met Leu Val
    210                 215                 220

Ala Asp Gln Ser Met Ala Glu Phe His Gly Ser Gly Leu Lys His Tyr
225                 230                 235                 240

Leu Leu Thr Leu Phe Ser Val Ala Ala Arg Leu Tyr Lys His Pro Ser
                245                 250                 255

Ile Arg Asn Ser Val Ser Leu Val Val Val Lys Ile Leu Val Ile His
                260                 265                 270

Asp Glu Gln Lys Gly Pro Glu Val Thr Ser Asn Ala Ala Leu Thr Leu
            275                 280                 285

Arg Asn Phe Cys Asn Trp Gln Lys Gln His Asn Pro Pro Ser Asp Arg
```

```
                290                 295                 300
Asp Ala Glu His Tyr Asp Thr Ala Ile Leu Phe Thr Arg Gln Asp Leu
305                 310                 315                 320

Cys Gly Ser Gln Thr Cys Asp Thr Leu Gly Met Ala Asp Val Gly Thr
                325                 330                 335

Val Cys Asp Pro Ser Arg Ser Cys Ser Val Ile Glu Asp Asp Gly Leu
                340                 345                 350

Gln Ala Ala Phe Thr Thr Ala His Glu Leu Gly His Val Phe Asn Met
                355                 360                 365

Pro His Asp Asp Ala Lys Gln Cys Ala Ser Leu Asn Gly Val Asn Gln
370                 375                 380

Asp Ser His Met Met Ala Ser Met Leu Ser Asn Leu Asp His Ser Gln
385                 390                 395                 400

Pro Trp Ser Pro Cys Ser Ala Tyr Met Ile Thr Ser Phe Leu Asp Asn
                405                 410                 415

Gly His Gly Glu Cys Leu Met Asp Lys Pro Gln Asn Pro Ile Gln Leu
                420                 425                 430

Pro Gly Asp Leu Pro Gly Thr Ser Tyr Asp Ala Asn Arg Gln Cys Gln
                435                 440                 445

Phe Thr Phe Gly Glu Asp Ser Lys His Cys Pro Asp Ala Ala Ser Thr
                450                 455                 460

Cys Ser Thr Leu Trp Cys Thr Gly Thr Ser Gly Gly Val Leu Val Cys
465                 470                 475                 480

Gln Thr Lys His Phe Pro Trp Ala Asp Gly Thr Ser Cys Gly Glu Gly
                485                 490                 495

Lys Trp Cys Ile Asn Gly Lys Cys Val Asn Lys Thr Asp Arg Lys His
                500                 505                 510

Phe Asp Thr Pro Phe His Gly Ser Trp Gly Met Trp Gly Pro Trp Gly
                515                 520                 525

Asp Cys Ser Arg Thr Cys Gly Gly Gly Val Gln Tyr Thr Met Arg Glu
                530                 535                 540

Cys Asp Asn Pro Val Pro Lys Asn Gly Gly Lys Tyr Cys Glu Gly Lys
545                 550                 555                 560

Arg Val Arg Tyr Arg Ser Cys Asn Leu Glu Asp Cys Pro Asp Asn Asn
                565                 570                 575

Gly Lys Thr Phe Arg Glu Glu Gln Cys Glu Ala His Asn Glu Phe Ser
                580                 585                 590

Lys Ala Ser Phe Gly Ser Gly Pro Ala Val Glu Trp Ile Pro Lys
                595                 600                 605

<210> SEQ ID NO 4
<211> LENGTH: 396
<212> TYPE: PRT
<213> ORGANISM: Artificial sequence
<220> FEATURE:
<223> OTHER INFORMATION: Synthetic amino acid sequence

<400> SEQUENCE: 4

Phe Val Ser Ser His Arg Tyr Val Glu Thr Met Leu Val Ala Asp Gln
1               5                   10                  15

Ser Met Ala Glu Phe His Gly Ser Gly Leu Lys His Tyr Leu Leu Thr
                20                  25                  30

Leu Phe Ser Val Ala Ala Arg Leu Tyr Lys His Pro Ser Ile Arg Asn
                35                  40                  45

Ser Val Ser Leu Val Val Val Lys Ile Leu Val Ile His Asp Glu Gln
```

```
            50                  55                  60
Lys Gly Pro Glu Val Thr Ser Asn Ala Ala Leu Thr Leu Arg Asn Phe
 65                      70                  75                  80

Cys Asn Trp Gln Lys Gln His Asn Pro Pro Ser Asp Arg Asp Ala Glu
                     85                  90                  95

His Tyr Asp Thr Ala Ile Leu Phe Thr Arg Gln Asp Leu Cys Gly Ser
                100                 105                 110

Gln Thr Cys Asp Thr Leu Gly Met Ala Asp Val Gly Thr Val Cys Asp
            115                 120                 125

Pro Ser Arg Ser Cys Ser Val Ile Glu Asp Asp Gly Leu Gln Ala Ala
        130                 135                 140

Phe Thr Thr Ala His Glu Leu Gly His Val Phe Asn Met Pro His Asp
145                 150                 155                 160

Asp Ala Lys Gln Cys Ala Ser Leu Asn Gly Val Asn Gln Asp Ser His
                165                 170                 175

Met Met Ala Ser Met Leu Ser Asn Leu Asp His Ser Gln Pro Trp Ser
                180                 185                 190

Pro Cys Ser Ala Tyr Met Ile Thr Ser Phe Leu Asp Asn Gly His Gly
            195                 200                 205

Glu Cys Leu Met Asp Lys Pro Gln Asn Pro Ile Gln Leu Pro Gly Asp
        210                 215                 220

Leu Pro Gly Thr Ser Tyr Asp Ala Asn Arg Gln Cys Gln Phe Thr Phe
225                 230                 235                 240

Gly Glu Asp Ser Lys His Cys Pro Asp Ala Ala Ser Thr Cys Ser Thr
                245                 250                 255

Leu Trp Cys Thr Gly Thr Ser Gly Gly Val Leu Val Cys Gln Thr Lys
                260                 265                 270

His Phe Pro Trp Ala Asp Gly Thr Ser Cys Gly Glu Gly Lys Trp Cys
            275                 280                 285

Ile Asn Gly Lys Cys Val Asn Lys Thr Asp Arg Lys His Phe Asp Thr
        290                 295                 300

Pro Phe His Gly Ser Trp Gly Met Trp Gly Pro Trp Gly Asp Cys Ser
305                 310                 315                 320

Arg Thr Cys Gly Gly Gly Val Gln Tyr Thr Met Arg Glu Cys Asp Asn
                325                 330                 335

Pro Val Pro Lys Asn Gly Gly Lys Tyr Cys Glu Gly Lys Arg Val Arg
                340                 345                 350

Tyr Arg Ser Cys Asn Leu Glu Asp Cys Pro Asp Asn Asn Gly Lys Thr
            355                 360                 365

Phe Arg Glu Glu Gln Cys Glu Ala His Asn Glu Phe Ser Lys Ala Ser
        370                 375                 380

Phe Gly Ser Gly Pro Ala Val Glu Trp Ile Pro Lys
385                 390                 395

<210> SEQ ID NO 5
<211> LENGTH: 605
<212> TYPE: PRT
<213> ORGANISM: Artificial sequence
<220> FEATURE:
<223> OTHER INFORMATION: Synthetic amino acid sequence

<400> SEQUENCE: 5

Met Leu Leu Cys Ala Arg Gly Ala His Gly Arg Pro Thr Glu Glu Asp
 1               5                  10                  15

Glu Glu Leu Val Leu Pro Ser Leu Glu Arg Ala Pro Gly His Asp Ser
```

```
            20                  25                  30
Thr Thr Thr Arg Leu Arg Leu Asp Ala Phe Gly Gln Gln Leu His Leu
        35                  40                  45
Lys Leu Gln Pro Asp Ser Gly Phe Leu Ala Pro Gly Phe Thr Leu Gln
    50                  55                  60
Thr Val Gly Arg Ser Pro Gly Ser Glu Ala Gln His Leu Asp Pro Thr
65                  70                  75                  80
Gly Asp Leu Ala His Cys Phe Tyr Ser Gly Thr Val Asn Gly Asp Pro
                85                  90                  95
Gly Ser Ala Ala Ala Leu Ser Leu Cys Glu Gly Val Arg Gly Ala Phe
            100                 105                 110
Tyr Leu Gln Gly Glu Glu Phe Phe Ile Gln Pro Ala Pro Gly Val Ala
        115                 120                 125
Thr Glu Arg Leu Ala Pro Ala Val Pro Glu Glu Ser Ser Ala Arg
    130                 135                 140
Pro Gln Phe His Ile Leu Arg Arg Arg Arg Gly Ser Gly Gly Ala
145                 150                 155                 160
Lys Cys Gly Val Met Asp Asp Glu Thr Leu Pro Thr Ser Asp Ser Arg
                165                 170                 175
Pro Glu Ser Gln Asn Thr Arg Asn Gln Trp Pro Val Arg Asp Pro Thr
            180                 185                 190
Pro Gln Asp Ala Gly Lys Pro Ser Gly Pro Gly Ser Ile Arg Lys Lys
        195                 200                 205
Arg Phe Val Ser Ser Pro Arg Tyr Val Glu Thr Met Leu Val Ala Asp
    210                 215                 220
Gln Ser Met Ala Asp Phe His Gly Ser Gly Leu Lys His Tyr Leu Leu
225                 230                 235                 240
Thr Leu Phe Ser Val Ala Ala Arg Phe Tyr Lys His Pro Ser Ile Arg
                245                 250                 255
Asn Ser Ile Ser Leu Val Val Val Lys Ile Leu Val Ile Tyr Glu Glu
            260                 265                 270
Gln Lys Gly Pro Glu Val Thr Ser Asn Ala Ala Leu Thr Leu Arg Asn
        275                 280                 285
Phe Cys Asn Trp Gln Lys Gln His Asn Ser Pro Ser Asp Arg Asp Pro
    290                 295                 300
Glu His Tyr Asp Thr Ala Ile Leu Phe Thr Arg Gln Asp Leu Cys Gly
305                 310                 315                 320
Ser His Thr Cys Asp Thr Leu Gly Met Ala Asp Val Gly Thr Val Cys
                325                 330                 335
Asp Pro Ser Arg Ser Cys Ser Val Ile Glu Asp Asp Gly Leu Gln Ala
            340                 345                 350
Ala Phe Thr Thr Ala His Glu Leu Gly His Val Phe Asn Met Pro His
        355                 360                 365
Asp Asp Ala Lys His Cys Ala Ser Leu Asn Gly Val Thr Gly Asp Ser
    370                 375                 380
His Leu Met Ala Ser Met Leu Ser Ser Leu Asp His Ser Gln Pro Trp
385                 390                 395                 400
Ser Pro Cys Ser Ala Tyr Met Val Thr Ser Phe Leu Asp Asn Gly His
                405                 410                 415
Gly Glu Cys Leu Met Asp Lys Pro Gln Asn Pro Ile Lys Leu Pro Ser
            420                 425                 430
Asp Leu Pro Gly Thr Leu Tyr Asp Ala Asn Arg Gln Cys Gln Phe Thr
        435                 440                 445
```

```
Phe Gly Glu Glu Ser Lys His Cys Pro Asp Ala Ala Ser Thr Cys Thr
    450                 455                 460

Thr Leu Trp Cys Thr Gly Thr Ser Gly Gly Leu Leu Val Cys Gln Thr
465                 470                 475                 480

Lys His Phe Pro Trp Ala Asp Gly Thr Ser Cys Gly Glu Gly Lys Trp
                485                 490                 495

Cys Val Ser Gly Lys Cys Val Asn Lys Thr Asp Met Lys His Phe Ala
            500                 505                 510

Thr Pro Val His Gly Ser Trp Gly Pro Trp Gly Pro Trp Gly Asp Cys
        515                 520                 525

Ser Arg Thr Cys Gly Gly Val Gln Tyr Thr Met Arg Glu Cys Asp
530                 535                 540

Asn Pro Val Pro Lys Asn Gly Gly Lys Tyr Cys Glu Gly Lys Arg Val
545                 550                 555                 560

Arg Tyr Arg Ser Cys Asn Ile Glu Asp Cys Pro Asp Asn Asn Gly Lys
                565                 570                 575

Thr Phe Arg Glu Glu Gln Cys Glu Ala His Asn Glu Phe Ser Lys Ala
                580                 585                 590

Ser Phe Gly Asn Glu Pro Thr Val Glu Trp Thr Pro Lys
        595                 600                 605

<210> SEQ ID NO 6
<211> LENGTH: 242
<212> TYPE: PRT
<213> ORGANISM: Artificial sequence
<220> FEATURE:
<223> OTHER INFORMATION: Synthetic amino acid sequence

<400> SEQUENCE: 6

Lys Ile Ser Gly Ser Val Thr Ser Ala Lys Pro Gly Tyr His Asp Ile
1               5                   10                  15

Ile Thr Ile Pro Thr Gly Ala Thr Asn Ile Glu Val Lys Gln Arg Asn
            20                  25                  30

Gln Arg Gly Ser Arg Asn Asn Gly Ser Phe Leu Ala Ile Lys Ala Ala
        35                  40                  45

Asp Gly Thr Tyr Ile Leu Asn Gly Asp Tyr Thr Leu Ser Thr Leu Glu
    50                  55                  60

Gln Asp Ile Met Tyr Lys Gly Val Val Leu Arg Tyr Ser Gly Ser Ser
65                  70                  75                  80

Ala Ala Leu Glu Arg Ile Arg Ser Phe Ser Pro Leu Lys Glu Pro Leu
                85                  90                  95

Thr Ile Gln Val Leu Thr Val Gly Asn Ala Leu Arg Pro Lys Ile Lys
            100                 105                 110

Tyr Thr Tyr Phe Val Lys Lys Lys Glu Ser Phe Asn Ala Ile Pro
        115                 120                 125

Thr Phe Ser Ala Trp Val Ile Glu Glu Trp Gly Glu Cys Ser Lys Ser
    130                 135                 140

Cys Glu Leu Gly Trp Gln Arg Arg Leu Val Glu Cys Arg Asp Ile Asn
145                 150                 155                 160

Gly Gln Pro Ala Ser Glu Cys Ala Lys Glu Val Lys Pro Ala Ser Thr
                165                 170                 175

Arg Pro Cys Ala Asp His Pro Cys Pro Gln Trp Gln Leu Gly Glu Trp
            180                 185                 190

Ser Ser Cys Ser Lys Thr Cys Gly Lys Gly Tyr Lys Lys Arg Ser Leu
        195                 200                 205
```

```
Lys Cys Leu Ser His Asp Gly Gly Val Leu Ser His Glu Ser Cys Asp
            210                 215                 220

Pro Leu Lys Lys Pro Lys His Phe Ile Asp Phe Cys Thr Met Ala Glu
225                 230                 235                 240

Cys Ser

<210> SEQ ID NO 7
<211> LENGTH: 138
<212> TYPE: PRT
<213> ORGANISM: Artificial sequence
<220> FEATURE:
<223> OTHER INFORMATION: Synthetic amino acid sequence

<400> SEQUENCE: 7

Asn Ala Leu Arg Pro Lys Ile Lys Tyr Thr Tyr Phe Val Lys Lys Lys
1               5                   10                  15

Lys Glu Ser Phe Asn Ala Ile Pro Thr Phe Ser Ala Trp Val Ile Glu
            20                  25                  30

Glu Trp Gly Glu Cys Ser Lys Ser Cys Glu Leu Gly Trp Gln Arg Arg
        35                  40                  45

Leu Val Glu Cys Arg Asp Ile Asn Gly Gln Pro Ala Ser Glu Cys Ala
    50                  55                  60

Lys Glu Val Lys Pro Ala Ser Thr Arg Pro Cys Ala Asp His Pro Cys
65                  70                  75                  80

Pro Gln Trp Gln Leu Gly Glu Trp Ser Ser Cys Ser Lys Thr Cys Gly
                85                  90                  95

Lys Gly Tyr Lys Lys Arg Ser Leu Lys Cys Leu Ser His Asp Gly Gly
            100                 105                 110

Val Leu Ser His Glu Ser Cys Asp Pro Leu Lys Lys Pro Lys His Phe
        115                 120                 125

Ile Asp Phe Cys Thr Met Ala Glu Cys Ser
        130                 135
```

MODULATION OF MUSCLE AND ADIPOCYTE DISTRIBUTION AND FATE

GOVERNMENT RIGHTS

This invention was made with Government support under contract DK073697 awarded by the National Institutes of Health. The Government has certain rights in the invention.

BACKGROUND OF THE INVENTION

The distribution of body mass into muscle and fat tissues has profound implications for the health of an individual. Many factors are known to be involved in the balance of adipocyte and muscle cell differentiation. For example, glucocorticoids such as cortisol, the natural hormone, or a multitude of synthetic cortisol analogues (including prednisone, hydrocortisone and dexamethasone) act via the glucocorticoid receptor (GR) to regulate a large array of tissues and cell specific actions in most cells in the body. Glucocorticoids play a critical role in regulating differentiation decisions both in vivo and ex vivo, favoring adipogenesis and inhibiting muscle formation. Androgen administration has also been shown to influence body composition, reducing fat mass but increasing muscle mass.

In the development of obesity, the increase in adipose tissue mass can be due to an increase in both the size and number of adipocytes. The increase in cell number can result of recruitment of preadipocytes from a population of multipotent stem cells or from sub-populations of cells resident in mature white adipose tissue (WAT). Bone marrow mesenchymal stem cells (MSCs) can differentiate into a variety of cell types including fat, muscle, cartilage, and bone. With aging, marrow adipogenesis accelerates in vivo, while the ability of MSCs to form bone decreases. It has been suggested that MSC precursors differentiate into adipose rather than bone with a reciprocal relationship, and thus may contribute to age-related body composition changes.

Fat redistribution in the elderly is associated with an increased risk for metabolic syndrome, including diabetes, hypertension, dyslipidemia, atherosclerosis and relatively increased intra-abdominal fat.

There is also a decline in muscle bulk and performance associated with normal aging, often resulting from gradual onset of sarcopenia. Although skeletal muscle has the capacity to regenerate itself, this process is not activated in the elderly. It has been suggested that age-related changes within skeletal muscle tissue and the host environment affect the proliferation and fusion of myoblasts in response to injury in old animals.

Deficient or poor functioning muscle are among the most devastating childhood health issues. Such muscle diseases are found in patients with a diverse set of congenital myopathies and muscular dystrophies, such as Duchenne Muscular Dystrophy (DMD), that together affect more than 1 in 3000 children. These disorders are usually associated with either inherited or spontaneous genetic mutations. Children with these disorders suffer from a wide spectrum of complications, frequently causing devastating morbidities with significantly premature mortality. The current lack of effective therapies and the frequency of fatalities underscore the urgent need for developing novel treatment strategies.

Muscle tissue in adult vertebrates regenerates from stem cells known as satellite cells or muscle stem cells (MuSCs). Satellite cells are distributed throughout muscle tissue and are mitotically quiescent in the absence of injury or disease, residing in an instructive, anatomically defined niche. In addition to satellite cells, cell types that might contribute to muscle regeneration include, but are not limited to, mesangioblasts, bone marrow derived cells, muscle interstitial cells, mesenchymal stem cells. See D. D. Cornelison et al. (2001) Dev Biol 239, 79; S. Fukada et al. (2004) Exp Cell Res 296, 245; D. Montarras et al. (2005) Science 309, 2064; S. Kuang et al. (2007) Cell 129, 999; M. Cerletti et al. (2008) Cell 134, 37; C. A. Collins et al. (2005) Cell 122, 289; A. Sacco et al. (2008) Nature 456, 502; R. I. Sherwood et al. (2004) Cell 119, 543; and Galvez et al. (2006) J Cell Biol. 174(2):231-43.

Tissue engineering seeks to repair or replace damaged or diseased tissues of the body by implanting combinations of cells, biomaterial scaffolds, biologically active molecules, and genes. An underlying premise of this approach is that exogenously introduced cells will improve the speed and extent of tissue repair. Adult MuSCs can be transplanted into injured or defective skeletal musculature to reconstitute muscle fibers and improve function, potentially providing for the therapeutic applications for MuSCs. However, a major obstacle to translating this technology is the lack of understanding about how differentiation decisions are determined and tools to control and promote these decisions for therapeutic benefits have not been developed. Advancing these areas could pioneer a variety of novel therapeutic approaches for individuals with impaired muscle mass or function, or to address an imbalance between muscle and adipose tissue.

SUMMARY OF THE INVENTION

Methods and compositions are provided for enhancing myogenesis in vitro or in vivo. In the methods of the invention, a stem or progenitor cell is contacted with an effective dose of an ADAMTS1 agonist. The ADAMTS1 agonist activates muscle stem cells or other muscle precursor cells, promotes differentiation and fusion into myofibers, and induces stem or progenitor cells to adopt a muscle fate. In some embodiments of the invention, the ADAMTS1 agonist is ADAMTS1 protein or an active fragment thereof. In other embodiments the ADAMTS1 agonist is an agent that increases expression of ADAMTS1, (e.g., by increasing transcription), or otherwise potentiates activity of ADAMTS1. Agonists include, without limitation, monoclonal antibodies, small molecules, chimeric proteins/peptides, bioactive polypeptides, and nucleic acids, e.g. nucleic acids that encode an ADAMTS1 protein or active fragment thereof.

In some embodiments the stem or progenitor cell is a muscle stem cell, including without limitation, a muscle satellite cell. In other embodiments the stem or progenitor cell is an adipocyte progenitor, including without limitation, preadipocytes and mesenchymal stem cells.

In some embodiments an effective dose of an ADAMTS1 agonist is administered to individual in need of increased muscle mass. The ADAMTS1 agonist acts to reduce adipogenesis and to increase myogenesis. Individuals in need of such treatment include individuals suffering from a myopathy, e.g. sarcopenia, cachexia, glucocorticoid induced myopathy, congenital myopathies, muscular dystrophy, myotonic dystrophy, etc., where the dose is effective to increase muscle mass or to reduce loss of muscle mass in the individual. Treatment may be continued for a period of time sufficient to provide a therapeutic effect, and may include a long-term maintenance dosing regimen. Individuals also include non-human mammals, e.g. livestock, including without limitation, equines, bovines, porcines, ursines, etc., for which increased muscle mass may be desired; pets, animal models for research purposes, and the like.

An individual in need of increased muscle mass may alternatively or in combination be treated by administration of muscle satellite cells that have been exposed ex vivo to an ADAMTS1 agonist, where the resulting cell population is then transplanted to the individual, which transplantation may involve targeted delivery of the cells to muscle tissue. Muscle stem/progenitor cells for this purpose may be allogeneic, autologous, etc.

In other embodiments an effective dose of an ADAMTS1 agonist is administered to individual in need of modifying metabolism, particularly modifying metabolism relating to use of insulin, including but not limited to individuals in need of decreased adipose tissue mass. The ADAMTS1 agonist acts to normalize insulin function; and can reduce adipogenesis and to increase myogenesis. Individuals in need of such treatment may include individuals suffering from conditions associated with excess adipose tissue and/or insulin resistance, e.g. obesity, Type 2 diabetes, metabolic syndrome, etc. Treatment may be continued for a period of time sufficient to provide a therapeutic effect, and may include a long term maintenance dosing regimen.

An ADAMTS1 agonist may be provided in a pharmaceutical formulation suitable for administration to a patient. Formulations of interest include, without limitation, formulations for systemic administration, including parental administration. Alternatively formulations of interest provide for substantial retention of the agonist in the tissue of interest.

The invention also provides agents that inhibit myogenesis in vitro or in vivo. In the methods of the invention, a stem or progenitor cell is contacted with an effective dose of an ADAMTS1 antagonist. The ADAMTS1 antagonist decreases muscle cell differentiation and fusion into myofibers. In some embodiments of the invention, the ADAMTS1 antagonist is ADAMTS1 C-terminal fragment, e.g. as disclosed herein. Antagonist also include, without limitation, monoclonal antibodies, small molecules, chimeric proteins/peptides, bioactive polypeptides, and nucleic acids, e.g. nucleic acids that encode an ADAMTS1 CTF fragment.

BRIEF DESCRIPTION OF THE DRAWINGS

The invention is best understood from the following detailed description when read in conjunction with the accompanying drawings. The patent or application file contains at least one drawing executed in color. Copies of this patent or patent application publication with color drawing(s) will be provided by the Office upon request and payment of the necessary fee. It is emphasized that, according to common practice, the various features of the drawings are not to-scale. On the contrary, the dimensions of the various features are arbitrarily expanded or reduced for clarity. Included in the drawings are the following figures.

FIG. 2A Immunohistochemistry of myosin heavy chain (MHC) in induced C2C12 cells supports that rADAM treatment enhances myogenesis relative to GST control treatment. FIG. 2B Expression (measured by RT-qPCR) of muscle specific markers in induced MuSCs treated with rADAM are increased relative to GST control treatment. FIG. 2C Muscle Mass.

FIG. 9A-9F. Adamts1 promotes muscle growth at postnatal stage. FIG. 9A, Adamts1 was inserted under the (AP2) promoter with an influenza hemagglutinin (HA) tag. FIG. 9B, Detection of ADAMTS1 overexpression by western blot with anti-HA antibody. FIG. 9C, Body weight is increased in transgenic mice with aging. FIG. 9D, Increased wet weights of transgenic tibialis anterior (TA) muscle and quadriceps skeletal muscles in 3 month old transgenic mice. FIG. 9E, Hematoxylin and eosin (H&E) staining shows larger myofibers in 3 month old transgenic mice. FIG. 9F, Quantitation of myofiber diameter reveals increased fiber size in 3 month old transgenic mice. Note: At least 3 pair of animals are used in the experiments. Wild type littermates were used as controls in all experiments.

FIG. 10A-10F. Adamts1 promotes satellite cell activation, leading to increased proliferation and differentiation. FIG. 10A, Recombinant proteins (control and Adamts1) purified from CHO supernatant by a poly-histidine (His) tag. FIG. 10B, Isolated myofibers were treated with recombinant proteins for 3 days in growth medium, then satellite cells were stained by pax7. FIG. 10C, The number of paired box protein (Pax7)-positive satellite cells were significantly increased in the myofibers treated with recombinant Adamts1. ***p<0.001. FIG. 10D, 5 week old mice were injected with 5-ethynyl-2-deoxyuridine (EDU) for 14 days, then the EDU-positive satellite cells per myofiber were counted. The EDU+ cells are significantly increased in the myofibers isolated from Adamts1 transgenic mice. FIG. 10E, Fluorescence activated cell sorting-purified satellite cells were cultured in vitro and treated with recombinant Adamts1 and control proteins isolated from CHO supernatant. Recombinant Adamts1 promotes satellite cell differentiation in vitro and myogenesis examined by qRT-PCR. FIG. 10F, FACS sorted satellite cells from wt and Adamts1 mice administered EDU for 14 days were plated and immediately assayed for the incorporation of EDU and the expression of myoD. SCs from Adamts1 transgenic mice have increased number of EDU incorporation, and are progressing along toward to myogenesis by expressing MyoD.

FIG. 11A-D. Incorporation of satellite cells into adjacent myofibers. Tibialis anterior muscle cross-section from wild type FIG. 11A and transgenic FIG. 11B mice treated daily with EDU for 14 days. EDU+ cells were highlighted by white arrows. Higher power magnification showing that EDU positive cells are myonuclei located beneath the myofiber membrane as delineated by dystrophin staining FIG. 11C. Quantification of EDU-positive myoblast cells FIG. 11D.

FIG. 12A, Adamts1 repressed Notch pathway in vivo as determined by expression of Notch1 and downstream targets of Hes1, Hey1. FIG. 12B, Adamts1 prevents Notch1 cleavage in the primary myoblasts isolated from mice. NICD (notch active form) is undetectable in the Adamts1 mice on the western blot in which actin serves as the loading control. TMIC: Notch transmembrane domain; NICD: Notch intracellular domain. Pax7 expression is decreased in transgenic mice compared to WT controls. FIG. 12C-12D, Induction of Adamts1 coordinated with repressed Notch pathway after injury in the WT animals by qRT-PCR FIG. 12C and western blot FIG. 12D.

FIG. 13A, Adamts1 binds to Notch1 by coimmunoprecipitation in 293T cells. FIG. 13B, Adamts1 blocks S2 cleavage of Notch1. FIG. 13A, Adamts1 binds to Notch1 ligand DLL1 in 293T cells and increases full-length DLL1 cleavage. FIG. 3D, Adamts1 increases DLL1 cleavage which is dependent on the metalloproteinase activity. FIG. 13E, Adamts1 interferes with binding of Notch1 and its ligand DLL1.

FIG. 14A-14C. Mapping of Adamts1 binding to Notch1 and DLL1 through the metalloproteinase domain. FIG. 14A, Diagram of serial deletion of Adamts1 proteins. FIG. 14B, Adamts1 interacts with Notch1. FIG. 14C, Adamts1 interacts with DLL1.

FIG. 15A-15E. The C-terminal fragment of ADAMTS1 is a natural inhibitor of myogenesis.

FIG. 16A-16C. Adamts1 inhibits adipogensis and promotes myogenesis in MSCs.

DESCRIPTION OF THE SPECIFIC EMBODIMENTS

Figure 1:
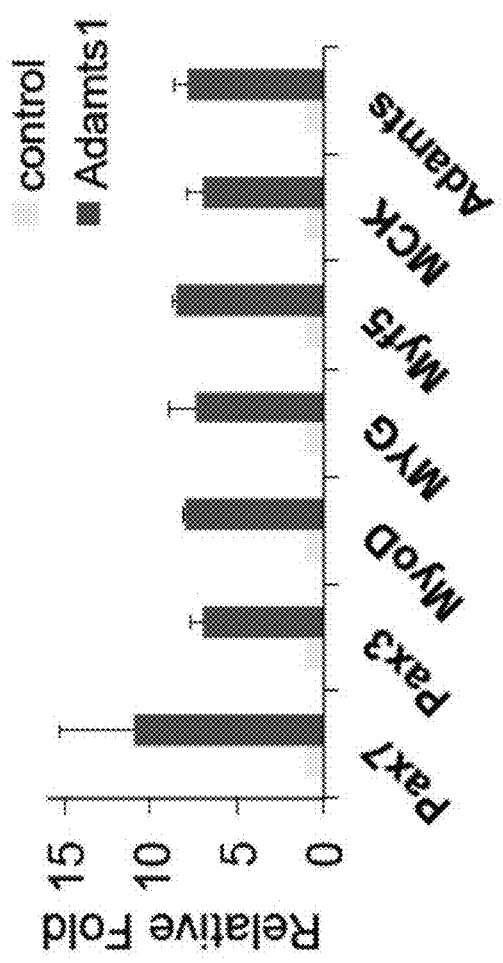
FIG. 1 is a graph depicting quantification using RT-qPCR of the levels of muscle lineage specific markers in MuSCs overexpressing Adamts1 relative to MuSCs with an empty vector control.

Methods and compositions are provided for enhancing the myogenic potential of stem and/or progenitor cells, including muscle satellite cells, pre-adipocytes, mesenchymal stem cells, etc. By administering agonists of ADAMTS1, muscle stem cells are activated, and stem cells are induced to adopt a muscle fate, thereby enhancing myogenesis.

In one embodiment of the invention, a subject in need of enhanced myogenesis is provided with an agent that is an agonist of the ADAMTS1, e.g. ADAMTS1 protein or an active fragment thereof. The agent may be provided systemically or locally. The agent may be provided in a pharmaceutical formulation suitable for administration to a patient. Formulations may provide for targeting to a specific organ and retention of the agent in the tissue of interest. The methods, kits, and pharmaceutical compositions of the invention, by increasing myogenesis, provide significant benefit to individuals suffering from muscle deficits and/or excess adipose tissue.

DEFINITIONS

In the description that follows, a number of terms conventionally used in the field of cell culture are utilized extensively. In order to provide a clear and consistent understanding of the specification and claims, and the scope to be given to such terms, the following definitions are provided.

It is to be understood that this invention is not limited to the particular methodology, protocols, cell lines, animal species or genera, and reagents described, as such may vary. It is also to be understood that the terminology used herein is for the purpose of describing particular embodiments only, and is not intended to limit the scope of the present invention, which will be limited only by the appended claims.

As used herein the singular forms "a", "an", and "the" include plural referents unless the context clearly dictates otherwise. Thus, for example, reference to "a cell" includes a plurality of such cells and reference to "the culture" includes reference to one or more cultures and equivalents thereof known to those skilled in the art, and so forth. All technical and scientific terms used herein have the same meaning as commonly understood to one of ordinary skill in the art to which this invention belongs unless clearly indicated otherwise.

ADAMTS is a family of proteins believed to be anchored to the extracellular matrix (ECM) through interactions with aggregan or other matrix components by one or more thrombospondin type 1 motifs. The genetic sequence of human ADAMTS1 may be found in Genbank, accession number NM_006988 and the reference protein sequence at NP_008919.

This family of metalloproteases has structural and functional properties related to but distinct from the ADAM family by the presence of several TSP-like domains in the C-terminal region and the lack of transmembrane domains. They are therefore secreted and associated with the ECM, which is proteolytically processed. The ADAMTS protein family is involved in various biologic processes, normal or pathologic. At least 19 ADAMTS enzymes had been characterized. They all share the same genomic organization, consisting of a signal sequence, a propeptide domain, a metalloproteinase domain containing a zinc-binding active-site motif (similar to that of the ADAM proteases), a disintegrin-like domain, a cysteine-rich region, and a variable number of THBS1 repeats.

ADAMTS1 is a secreted protein that has an N-terminal signal peptide, a zinc metalloprotease domain containing a zinc-binding site, and a cysteine-rich region containing 2 putative disintegrin loops. The C terminus of ADAMTS1 has 3 heparin-binding thrombospondin domains with 6 cys and 3 trp residues. A 4.6-kb ADAMTS1 transcript has been detected in all tissues tested, with highest expression in adrenal, heart, and placenta, followed by skeletal muscle, thyroid, stomach, and liver. ADAMTS1 is expressed as a 110-kD protein, an 85-kD protein after cleavage at the subtilisin site, or as a 67-kD protein, which is most abundant, generated by an additional processing event.

Relative to SEQ ID NO:1, or the Genbank reference human protein sequence, the ADAMTS1 signal peptide includes amino acid residues 1-49. The propeptide comprises residues 50-252. For the purposes of the invention, a full length ADAMTS1 protein may refer to amino acid residues 1-967; amino acid residues 50-967, amino acid residues 253-967, etc. The metalloprotease region comprises amino acid residues 258-463. The cysteine rich region comprises amino acid residues 468-548. The thrombospondin repeat regions comprise, respectively, residues 562-614; 858-910 and 912-967. The spacer region comprises residues 725-829.

The full length human ADAMTS1 protein has the amino acid sequence (SEQ ID NO:1):

MQRAVPEGFGRRKLGSDMGNAERAPGSRSFGPVPTLLLLAAALLAVSDAL

GRPSEEDEELVVPELERAPGHGTTRLRLHAFDQQLDLELRPDSSFLAPGF

TLQNVGRKSGSETPLPETDLAHCFYSGTVNGDPSSAAALSLCEGVRGAFY

LLGEAYFIQPLPAASERLATAAPGEKPPAPLQFHLLRRNRQGDVGGTCGV

VDDEPRPTGKAETEDEDEGTEGEDEGAQWSPQDPALQGVGQPTGTGSIRK

KRFVSSHRYVETMLVADQSMAEFHGSGLKHYLLTLFSVAARLYKHPSIRN

SVSLVVVKILVIHDEQKGPEVTSNAALTLRNFCNWQKQHNPPSDRDAEHY

DTAILFTRQDLCGSQTCDTLGMADVGTVCDPSRSCSVIEDDGLQAAFTTA

HELGHVFNMPHDDAKQCASLNGVNQDSHMMASMLSNLDHSQPWSPCSAYM

ITSFLDNGHGECLMDKPQNPIQLPGDLPGTSYDANRQCQFTFGEDSKHCP

DAASTCSTLWCTGTSGGVLVCQTKHFPWADGTSCGEGKWCINGKCVNKTD

RKHFDTPFHGSWGMWGPWGDCSRTCGGGVQYTMRECDNPVPKNGGKYCEG

KRVRYRSCNLEDCPDNNGKTFREEQCEAHNEFSKASFGSGPAVEWIPKYA

GVSPKDRCKLICQAKGIGYFFVLQPKVVDGTPCSPDSTSVCVQGQCVKAG

CDRIIDSKKKFDKCGVCGGNGSTCKKISGSVTSAKPGYHDIITIPTGATN

IEVKQRNQRGSRNNGSFLAIKAADGTYILNGDYTLSTLEQDIMYKGVVLR

YSGSSAALERIRSFSPLKEPLTIQVLTVGNALRPKIKYTYFVKKKKESFN

AIPTFSAWVIEEWGECSKSCELGWQRRLVECRDINGQPASECAKEVKPAS

TRPCADHPCPQWQLGEWSSCSKTCGKGYKKRSLKCLSHDGGVLSHESCDP

LKKPKHFIDFCTMAECS

The mouse counterpart fragment has the amino acid sequence (SEQ ID NO:2)

MQPKVPLGSRKQKPCSDMGDVQRAARSRGSLSAHMLLLLLASITMLLCAR

GAHGRPTEEDEELVLPSLERAPGHDSTTTRLRLDAFGQQLHLKLQPDSGF

LAPGFTLQTVGRSPGSEAQHLDPTGDLAHCFYSGTVNGDPGSAAALSLCE

GVRGAFYLQGEEFFIQPAPGVATERLAPAVPEEESSARPQFHILRRRRRG

SGGAKCGVMDDETLPTSDSRPESQNTRNQWPVRDPTPQDAGKPSGPGSIR

KKRFVSSPRYVETMLVADQSMADFHGSGLKHYLLTLFSVAARFYKHPSIR

NSISLVVVKILVIYEEQKGPEVTSNAALTLRNFCNWQKQHNSPSDRDPEH

YDTAILFTRQDLCGSHTCDTLGMADVGTVCDPSRSCSVIEDDGLQAAFTT

AHELGHVFNMPHDDAKHCASLNGVTGDSHLMASMLSSLDHSQPWSPCSAY

MVTSFLDNGHGECLMDKPQNPIKLPSDLPGTLYDANRQCQFTFGEESKHC

PDAASTCTTLWCTGTSGGLLVCQTKHFPWADGTSCGEGKWCVSGKCVNKT

DMKHFATPVHGSWGPWGPWGDCSRTCGGGVQYTMRECDNPVPKNGGKYCE

GKRVRYRSCNIEDCPDNNGKTFREEQCEAHNEFSKASFGNEPTVEWTPKY

AGVSPKDRCKLTCEAKGIGYFFVLQPKVVDGTPCSPDSTSVCVQGQCVKA

GCDRIIDSKKKFDKCGVCGGNGSTCKKMSGIVTSTRPGYHDIVTIPAGAT

NIEVKHRNQRGSRNNGSFLAIRAADGTYILNGNFTLSTLEQDLTYKGTVL

RYSGSSAALERIRSFSPLKEPLTIQVLMVGHALRPKIKFTYFKKKKK

An exemplary active fragment of the human protein useful for promoting myogenesis has the amino acid sequence (SEQ ID NO:3):

ALLAVSDALGRPSEEDEELVVPELERAPGHGTTRLRLHAFDQQLDLELRP

DSSFLAPGFTLQNVGRKSGSETPLPETDLAHCFYSGTVNGDPSSAAALSL

CEGVRGAFYLLGEAYFIQPLPAASERLATAAPGEKPPAPLQFHLLRRNRQ

GDVGGTCGVVDDEPRPTGKAETEDEDEGTEGEDEGAQWSPQDPALQGVGQ

PTGTGSIRKKRFVSSHRYVETMLVADQSMAEFHGSGLKHYLLTLFSVAAR

LYKHPSIRNSVSLVVVKILVIHDEQKGPEVTSNAALTLRNFCNWQKQHNP

PSDRDAEHYDTAILFTRQDLCGSQTCDTLGMADVGTVCDPSRSCSVIEDD

GLQAAFTTAHELGHVFNMPHDDAKQCASLNGVNQDSHMMASMLSNLDHSQ

PWSPCSAYMITSFLDNGHGECLMDKPQNPIQLPGDLPGTSYDANRQCQFT

FGEDSKHCPDAASTCSTLWCTGTSGGVLVCQTKHFPWADGTSCGEGKWCI

NGKCVNKTDRKHFDTPFHGSWGMWGPWGDCSRTCGGGVQYTMRECDNPVP

KNGGKYCEGKRVRYRSCNLEDCPDNNGKTFREEQCEAHNEFSKASFGSGP

AVEWIPK

An alternative active fragment has the pro-peptide deleted, shown in SEQ ID NO:4

FVSSHRYVETMLVADQSMAEFHGSGLKHYLLTLFSVAARLYKHPSIRNSV

SLVVVKILVIHDEQKGPEVTSNAALTLRNFCNWQKQHNPPSDRDAEHYDT

AILFTRQDLCGSQTCDTLGMADVGTVCDPSRSCSVIEDDGLQAAFTTAHE

LGHVFNMPHDDAKQCASLNGVNQDSHMMASMLSNLDHSQPWSPCSAYMIT

SFLDNGHGECLMDKPQNPIQLPGDLPGTSYDANRQCQFTFGEDSKHCPDA

ASTCSTLWCTGTSGGVLVCQTKHFPWADGTSCGEGKWCINGKCVNKTDRK

HFDTPFHGSWGMWGPWGDCSRTCGGGVQYTMRECDNPVPKNGGKYCEGKR

VRYRSCNLEDCPDNNGKTFREEQCEAHNEFSKASFGSGPAVEWIPK

The mouse counterpart active fragment has the amino acid sequence:

(SEQ ID NO: 5)
MLLCARGAHGRPTEEDEELVLPSLERAPGHDSTTTRLRLDAFGQQLHLKL

QPDSGFLAPGFTLQTVGRSPGSEAQHLDPTGDLAHCFYSGTVNGDPGSAA

ALSLCEGVRGAFYLQGEEFFIQPAPGVATERLAPAVPEEESSARPQFHIL

RRRRRGSGGAKCGVMDDETLPTSDSRPESQNTRNQWPVRDPTPQDAGKPS

GPGSIRKKRFVSSPRYVETMLVADQSMADFHGSGLKHYLLTLFSVAARFY

KHPSIRNSISLVVVKILVIYEEQKGPEVTSNAALTLRNFCNWQKQHNSPS

-continued

```
DRDPEHYDTAILFTRQDLCGSHTCDTLGMADVGTVCDPSRSCSVIEDDGL

QAAFTTAHELGHVFNMPHDDAKHCASLNGVTGDSHLMASMLSSLDHSQPW

SPCSAYMVTSFLDNGHGECLMDKPQNPIKLPSDLPGTLYDANRQCQFTFG

EESKHCPDAASTCTTLWCTGTSGGLLVCQTKHFPWADGTSCGEGKWCVSG

KCVNKTDMKHFATPVHGSWGPWGPWGDCSRTCGGGVQYTMRECDNPVPKN

GGKYCEGKRVRYRSCNIEDCPDNNGKTFREEQCEAHNEFSKASFGNEPTV

EWTPK
```

The antagonist, C-terminal fragment of the human protein has the sequence (SEQ ID NO:6):

```
KISGSVTSAKPGYHDIITIPTGATNIEVKQRNQRGSRNNGSFLAIKAADG

TYILNGDYTLSTLEQDIMYKGVVLRYSGSSAALERIRSFSPLKEPLTIQV

LTVGNALRPKIKYTYFVKKKKESFNAIPTFSAWVIEEWGECSKSCELGWQ

RRLVECRDINGQPASECAKEVKPASTRPCADHPCPQWQLGEWSSCSKTCG

KGYKKRSLKCLSHDGGVLSHESCDPLKKPKHFIDFCTMAECS
``` or SEQ ID NO:7

```
NALRPKIKYTYFVKKKKESFNAIPTFSAWVIEEWGECSKSCELGWQRRLV

ECRDINGQPASECAKEVKPASTRPCADHPCPQWQLGEWSSCSKTCGKGYK

KRSLKCLSHDGGVLSHESCDPLKKPKHFIDFCTMAECS
```

Polypeptides useful as agonists in the methods of the invention include, without limitation, those set forth in SEQ ID NO:1-5. Polypeptides useful as antagonists include, without limitation, those set forth in SEQ ID NO:6-7, corresponding to the C-terminal fragment of ADAMTS1.

Active ADAMTS1 agonist fragments, for promoting myogenesis, have a sequence corresponding to all or part of the N-terminal fragment of ADAMTS1. The fragments optionally include the signal sequence, and/or the propeptide sequence, but such is not required for activity. Active fragments for promoting myogenesis generally comprise at least the metalloprotease domain, i.e. SEQ ID NO:1, residues 258-463, although it should be noted that an active protease is not required for the myogenesis promoting activity. The pro-myogenic fragment may optionally comprise the cysteine rich region, amino acid residues 468-548; and the first thrombospondin repeat region, residues 562-614, up to the full-length protein.

Active antagonist, anti-myogenic fragments comprise the C-terminal portion of ADAMTS1, for example from the spacer region, residues 725-829, to the N-terminus at residue 967. Thus, antagonist fragments include, without limitation, residues 725-967, residues 829-967, etc.

In general, the term "polypeptide" as used herein refers to both the full length polypeptide, as well as portions or fragments thereof. "Polypeptides" also includes variants of the naturally occurring proteins, where such variants are homologous or substantially similar to the naturally occurring protein, and can be of an origin of the same or different species as the naturally occurring protein. In general, variant polypeptides have a sequence that has at least about 90%, usually at least about 95%, and more usually at least about 98 to 99% sequence identity with a polypeptide described herein. The variant polypeptides can be naturally or non-naturally glycosylated, i.e., the polypeptide has a glycosylation pattern that differs from the glycosylation pattern found in the corresponding naturally occurring protein. A "functional derivative" of a native polypeptide is a polypeptide having a qualitative biological property in common with a native polypeptide. "Functional derivatives" include, but are not limited to, fragments and derivatives of a native polypeptide, provided that they have a biological activity in common with a corresponding native polypeptide. The term "derivative" encompasses both amino acid sequence variants of polypeptides and covalent modifications thereof.

Fragments of ADAMTS1 polypeptides, particularly biologically active fragments and/or fragments corresponding to functional domains, are of interest. Fragments of interest will typically be at least about 200 aa to at least about 700 aa in length, usually at least about 400 aa in length, and can be as long as about 500 aa in length, about 600 aa in length or longer including about 607 aa in length, but will usually not exceed the full length protein except where it is a fusion protein, where the fragment will have a stretch of amino acids that is identical to a polypeptide provided herein, or a homolog thereof. Fragments may be truncated at one or both of the amino and carboxy terminus. A fragment "at least about 500 aa in length", for example, is intended to include 500 or more contiguous amino acids from, for example, a polypeptide sequence provided herein. In this context "about" includes the particularly recited value or a value larger or smaller by several (5, 4, 3, 2, or 1) amino acids.

The sequence of ADAMTS1 polypeptides may be altered in various ways known in the art to generate targeted changes in sequence. The sequence changes may be substitutions, insertions or deletions. Such alterations may be used to alter properties of the protein, by affecting the stability, specificity, etc. Techniques for in vitro mutagenesis of cloned genes are known. Examples of protocols for scanning mutations may be found in Gustin et al., Biotechniques 14:22 (1993); Barany, Gene 37:111-23 (1985); Colicelli et al., Mol Gen Genet 199:537-9 (1985); and Prentki et al., Gene 29:303-13 (1984). Methods for site specific mutagenesis can be found in Sambrook et al., Molecular Cloning: A Laboratory Manual, CSH Press 1989, pp. 15.3-15.108; Weiner et al., Gene 126:35-41 (1993); Sayers et al., Biotechniques 13:592-6 (1992); Jones and Winistorfer, Biotechniques 12:528-30 (1992); Barton et al., Nucleic Acids Res 18:7349-55 (1990); Marotti and Tomich, Gene Anal Tech 6:67-70 (1989); and Zhu Anal Biochem 177:120-4 (1989).

The polypeptides may be joined to a wide variety of other oligopeptides or proteins for a variety of purposes. By providing for expression of the subject polypeptides, various post-expression modifications may be achieved. For example, by employing the appropriate coding sequences, one may provide farnesylation or prenylation. The polypeptides may be PEGylated, where the polyethyleneoxy group provides for enhanced lifetime in the blood stream. The polypeptides may also be combined with other proteins, such as the Fc of an IgG isotype or the like, or with specific binding agents that allow targeting to specific moieties on a target cell.

A "chimeric" polypeptide is a polypeptide comprising a polypeptide or fragment (e.g., one or more domains) thereof fused or bonded to heterologous polypeptide. Examples of chimeric polypeptides include immunoadhesins, which combine a portion of the polypeptide with an immunoglobulin sequence, and epitope tagged polypeptides, which comprise a polypeptide or portion thereof fused to a "tag polypeptide". The tag polypeptide has enough residues to provide an epitope against which an antibody can be made, yet is short enough such that it does not interfere with biological activity of the polypeptide. Suitable tag polypeptides generally have at least six amino acid residues and usually between about 6-60 amino acid residues.

An ADAMTS1 polypeptide can be recovered and purified from recombinant cell cultures by well-known methods including ammonium sulfate or ethanol precipitation, acid extraction, anion or cation exchange chromatography, phosphocellulose chromatography, hydrophobic interaction chromatography, affinity chromatography, hydroxyapatite chromatography and lectin chromatography. For the most part, the compositions which are used will comprise at least 20% by weight of the desired product, more usually at least about 75% by weight, preferably at least about 95% by weight, and for therapeutic purposes, usually at least about 99.5% by weight, in relation to contaminants related to the method of preparation of the product and its purification. Usually, the percentages will be based upon total protein. Polypeptides can also be recovered from: products purified from natural sources, including bodily fluids, tissues and cells, whether directly isolated or cultured; products of chemical synthetic procedures; and products produced by recombinant techniques from a prokaryotic or eukaryotic host, including, for example, bacterial, yeast higher plant, insect, and mammalian cells.

The invention includes nucleic acids encoding the peptides of the invention. ADAMTS1 coding sequences can be generated by methods known in the art, e.g. by in vitro synthesis, recombinant methods, etc. to provide a coding sequence to corresponds to a ADAMTS1 polypeptide that can serve as an intermediate in the production of the ADAMTS1 polypeptide. Using the known genetic code, one can produce a suitable coding sequence. Double or single stranded fragments can be obtained from the DNA sequence by chemically synthesizing oligonucleotides in accordance with conventional methods, by restriction enzyme digestion, by PCR amplification, etc.

ADAMTS1 encoding nucleic acids can be provided as a linear molecule or within a circular molecule, and can be provided within autonomously replicating molecules (vectors) or within molecules without replication sequences. Expression of the nucleic acids can be regulated by their own or by other regulatory sequences known in the art. The nucleic acids can be introduced into suitable host cells using a variety of techniques available in the art, such as transferrin polycation-mediated DNA transfer, transfection with naked or encapsulated nucleic acids, liposome-mediated DNA transfer, intracellular transportation of DNA-coated latex beads, protoplast fusion, viral infection, electroporation, gene gun, calcium phosphate-mediated transfection, and the like.

Expression vectors may be used to introduce a ADAMTS1 coding sequence into a cell. Such vectors generally have convenient restriction sites located near the promoter sequence to provide for the insertion of nucleic acid sequences. Transcription cassettes may be prepared comprising a transcription initiation region, the target gene or fragment thereof, and a transcriptional termination region. The transcription cassettes may be introduced into a variety of vectors, e.g. plasmid; retrovirus, e.g. lentivirus; adenovirus; and the like, where the vectors are able to transiently or stably be maintained in the cells, usually for a period of at least about one day, more usually for a period of at least about several days to several weeks.

ADAMTS1 agonist. As used herein and as demonstrated in the Examples, agents that aid in increasing myogenesis from stem and progenitor cells are those that activate the ADAMTS1 signaling pathway. Included specifically as agonists are ADAMTS1 polypeptides, active fragments thereof, and polynucleotides that encode such polypeptides, and, for example, are expressed in a stem or progenitor cell of interest. Also included are mimetics, agonist antibodies, and the like.

Agents of interest may interact directly with ADAMTS1, e.g. antibodies, native ligands, synthetic ligands, and the like, or may activate downstream events. Agonists of interest include binding partners that bind to, and activate ADAMTS1 signaling pathway. In one embodiment, the specific binding member is an antibody. The term "antibody" or "antibody moiety" is intended to include any polypeptide chain-containing molecular structure with a specific shape that fits to and recognizes an epitope, where one or more non-covalent binding interactions stabilize the complex between the molecular structure and the epitope.

ADAMTS1 Antagonist.

As used herein and as demonstrated in the Examples, agents that decrease myogenesis from stem and progenitor cells are those that inhibit the ADAMTS1 signaling pathway. Included specifically as agonists are ADAMTS1 C-terminal fragment polypeptides for example as set forth in SEQ ID NO:6, active fragments thereof, and polynucleotides that encode such polypeptides, and, for example, are expressed in a stem or progenitor cell of interest. Also included are antagonist antibodies, small molecules, and the like.

Agents of interest may interact directly with ADAMTS1, e.g. antibodies, native ligands, synthetic ligands, and the like, or may activate downstream events. Agonists of interest include binding partners that bind to, and inhibit ADAMTS1 signaling pathway. In one embodiment, the specific binding member is an antibody. The term "antibody" or "antibody moiety" is intended to include any polypeptide chain-containing molecular structure with a specific shape that fits to and recognizes an epitope, where one or more non-covalent binding interactions stabilize the complex between the molecular structure and the epitope.

Stem Cell:

The term stem cell is used herein primarily to refer to a cell that has the ability both to self-renew, and to generate differentiated progeny (see Morrison et al. (1997) Cell 88:287-298). For example, the cell can be a mammalian or non-mammalian cell. Mammals include laboratory models, e.g. rats, mice, rabbits, etc., farm animals and other domesticated animals such as horses, cats, pigs, dogs, sheep, etc.; and particularly include primates, more particularly humans. Generally, stem cells also have one or more of the following properties: an ability to undergo asynchronous, or asymmetric replication, that is where the two daughter cells after division can have different phenotypes; extensive self-renewal capacity; capacity for existence in a mitotically quiescent form; and clonal regeneration of all the tissue in which they exist. "Progenitor cells" differ from stem cells in that they typically do not have the extensive self-renewal capacity, and often can only regenerate a subset of the lineages in the tissue from which they derive.

Stem cells may be characterized by both the presence of markers associated with specific epitopes identified by antibodies and the absence of certain markers as identified by the lack of binding of specific antibodies. Stem cells may also be identified by functional assays both in vitro and in vivo, particularly assays relating to the ability of stem cells to give rise to multiple differentiated progeny. Stem cells include, but are not limited to, embryonic cells, certain germ cells, embryonic stem cells, induced pluripotent stem cells, multipotent stem cells, and the like, as well as somatic stem cells.

Somatic stem cells reside in differentiated tissue, but retain the properties of self-renewal and the ability to give rise to multiple cell types, usually cell types typical of the tissue in which the stem cells are found. Numerous examples of somatic stem cells are known to those of skill in the art, including, but not limited to, muscle stem cells (including without limitation satellite cells as described above), mesenchymal stem cells, and preadipocytes.

The term "muscle cell" as used herein refers to any cell which contributes to muscle tissue. Myoblasts, satellite cells, myotubes, and myofibril tissues are all included in the term "muscle cells". Muscle cell effects may be induced within skeletal, cardiac and smooth muscles, usually within skeletal muscle. Muscle tissue in adult vertebrates regenerate from reserve myoblasts called "satellite cells", or mesangioblasts, bone marrow derived cells, muscle interstitial cells, mesenchymal stem cells, etc. Satellite cells are distributed throughout muscle tissue and are mitotically quiescent in the absence of injury or disease. Following muscle injury or during recovery from disease, satellite cells will reenter the cell cycle, proliferate and 1) enter existing muscle fibers or 2) undergo differentiation into multinucleate myotubes, which form new muscle fiber. The myoblasts ultimately yield replacement muscle fibers or fuse into existing muscle fibers, thereby increasing fiber girth by the synthesis of contractile apparatus components. This process is illustrated, for example, by the nearly complete regeneration which occurs in mammals following induced muscle fiber degeneration; the muscle progenitor cells proliferate and fuse together regenerating muscle fibers. One example of muscle stem cells is cells characterized as $CD45^-$, $CD11b^-$, $CD31^-$, $Sca1^-$, $\alpha 7$ integrin$^+$, and $CD34^+$.

Muscle regeneration, or myogenesis, as used herein refers to the process by which new muscle fibers form from muscle progenitor cells. An effective dose of a therapeutic composition will usually confer an increase in the number of new fibers by at least 1%, more preferably by at least 20%, and most preferably by at least 50%. The growth of muscle may occur by the increase in the fiber size and/or by increasing the number of fibers. The growth of muscle may be measured by an increase in wet weight, an increase in protein content, an increase in the number of muscle fibers, an increase in muscle fiber diameter; etc. An increase in growth of a muscle fiber can be defined as an increase in the diameter where the diameter is defined as the minor axis of ellipsis of the cross section. For in vivo effects, an ADAMTS1 agonist can be administered to an individual in vivo; or stem/progenitor cells can be manipulated ex vivo and transplanted to a recipient for generation of muscle tissue, where the cells can be delivered in a suitable medium, etc.

Muscle regeneration may also be monitored by the mitotic index of muscle. For example, cells may be exposed to a labeling agent for a time equivalent to two doubling times. The mitotic index is the fraction of cells in the culture which have labeled nuclei when grown in the presence of a tracer which only incorporates during S phase (i.e., BrdU) and the doubling time is defined as the average S time required for the number of cells in the culture to increase by a factor of two. Alternatively, activation in vivo may be detected by monitoring the appearance of the intermediate filament vimentin by immunological or RNA analysis methods. When vimentin is assayed, a useful activator may cause expression of detectable levels of vimentin in the muscle tissue when the therapeutically useful dosage is provided. Productive muscle regeneration may be also monitored by an increase in muscle strength and agility.

Muscle regeneration may also be measured by quantitation of myogenesis, i.e. fusion of myoblasts to yield myotubes. An effect on myogenesis results in an increase in the fusion of myoblasts and the enablement of the muscle differentiation program. For example, the myogenesis may be measured by the fraction of nuclei present in multinucleated cells in relative to the total number of nuclei present. Myogenesis may also be determined by assaying the number of nuclei per area in myotubes or by measurement of the levels of muscle specific protein by Western analysis. Also, nuclei of newly formed mytubes are centrally located.

The survival of muscle fibers may refer to the prevention of loss of muscle fibers as evidenced by necrosis or apoptosis or the prevention of other mechanisms of muscle fiber loss. Muscles can be lost from injury, atrophy, and the like, where atrophy of muscle refers to a significant loss in muscle fiber girth.

The term "adipocyte" refers to a fat cell, usually in this context a white fat cell. In adult life there can be a turnover in fat cells as a result of acquisition of new adipocytes from adult adipose tissue progenitors (mesenchymal stem cells and preadipocytes) via adipogenesis. Conditions in which adipogenesis is undesirable can include obesity, metabolic syndrome and Type 2 diabetes; and the like. It is shown herein that an agonist of ADAMTS1 signaling, e.g. ADAMTS1 protein or an active fragment thereof, acts to block adipogenesis. Administration of the agonist in an effective dose to an individual in need thereof provides for an altered ratio of muscle and fat, where adipogenesis is decreased and myogenesis is increased.

Adipocyte progenitor cells in vivo have been described in the art as including mesenchymal stem cells (MSC), multipotent adipose progenitor cells, pre-adipocytes and early adipocytes. A cell may be classified as an MSC if it shows plastic adherent properties under normal culture conditions and has a fibroblast-like morphology, can undergo osteogenic, adipogenic and chondrogenic differentiation ex-vivo; and is positive for CD73, CD90 and CD105, while lacking the expression of CD11 b, CD14, CD19, CD34, CD45, CD79a and HLA-DR surface markers. Multipotent adipose progenitors have been described as Lin−, CD29+, CD34+, CD24+(see Lin et al. (2008) Stem Cells Dev. 17:1053-1063). Early adipocyte progenitor cells have been described as $Lin^-$, $CD29^+$, $CD34^+$, $CD24^+$ (see Rodeheffer et al. (2008) Cell 135:240-249). resident in adult WAT. Immature adipocyte or preadipocytes have been described as aP2+/CD68−. Adipose tissue-derived stem cells (ADSC) are routinely isolated from the stromal vascular fraction (SVF) of homogenized adipose tissue. Freshly isolated ADSC display surface markers that differ from those of cultured ADSC, but both cell preparations are capable of multipotential differentiation.

The term "cell culture" or "culture" means the maintenance of cells in an artificial, in vitro environment. Culture conditions may include, without limitation, a specifically dimensioned container, e.g. flask, roller bottle, plate, 96 well plate, etc.; culture medium comprising suitable factors and nutrients for growth of the desired cell type; and a substrate on the surface of the container or on particles suspended in the culture medium. By "container" is meant a glass, plastic, or metal vessel that can provide an aseptic environment for culturing cells.

The terms "primary culture" and "primary cells" refer to cells derived from intact or dissociated tissues or organs, or fragments thereof. A culture is considered primary until it is passed (or subcultured) after which it is termed a "cell line" or a "cell strain." The term "cell line" does not imply homogeneity or the degree to which a culture has been characterized. A cell line is termed "clonal cell line" or "clone" if it is derived from a single cell in a population of cultured cells. Primary cells can be obtained directly (or indirectly) from a human or animal or from adult or fetal tissue, including blood (e.g., cord blood), muscle tissue, adipose tissue, etc. The primary cells may comprise a primary cell line, such as, but not limited to, a population of muscle satellite cells.

Culture Medium:

Cells are grown in vitro in an appropriate liquid nutrient medium. Generally, the seeding level will be at least about 10 cells/ml, more usually at least about 100 cells/ml and generally not more than about $10^5$ cells/ml, usually not more than about $10^4$ cells/ml. Cells may be cultured singly or in groups.

Various media are commercially available and may be used, including, but not limited to, Ex vivo serum free medium, Dulbecco's Modified Eagle Medium (DMEM), RPMI, Iscove's medium, etc. The medium may be supplemented with serum or with defined additives. For example, a medium may include 5%, 10%, 15% serum, as known in the art. Appropriate antibiotics to prevent bacterial growth and other additives, including, but not limited to, pyruvate (0.1-5 mM), glutamine (0.5-5 mM), 2-mercaptoethanol ($1-10\times10^{-5}$ M) may also be included. The medium may be any conventional culture medium, generally supplemented with additives, including, but not limited to, iron-saturated transferrin, human serum albumin, soy bean lipids, linoleic acid, cholesterol, alpha thioglycerol, crystalline bovine hemin, etc., that allow for the growth of cells. In some circumstances, proliferative factors that do not alter cellular differentiation may be included in the cultures, e.g. c-kit ligand, LIF, and the like. Medium of interest will typically include at least one ADAMTS1 agonist, although for screening purposes control cultures will also be utilized, and the cultures may have a sub-optimal dose of the agonist.

Cultured cells may be modified prior to, or during the culture period. In some embodiments, the cultured cell is a stem cell. In some embodiments, the stem cells are genetically modified for therapeutic or experimental purposes, e.g. by introducing factors that provide for oncogenic transformation, by introducing therapeutic genes such as dystrophin, and the like.

The terms "grafting", "engrafting", and "transplanting" and "graft" and "transplantation" as used herein refer to the process by which stem cells or other cells, e.g. cells treated with an agonist of ADAMTS1 signaling, e.g. an ADAMTS1 protein or active fragment thereof, according to the present disclosure, are delivered to the site where the cells are intended to exhibit an effect, such as, but not limited to, repairing damage or treating the effects of muscle and/or other damage caused by birth defects, stroke, disease, physical injury or trauma or genetic damage or environmental insult to the body, caused by, for example, disease, an accident or other activity. For example, the term "cell engraftment" as used herein can refer to the process by which cells such as, but not limited to, muscle stem cells, are delivered to, and become incorporated into, a differentiated tissue such as a muscle, and become a part of that tissue. For example, muscle cells, when delivered to a muscle tissue, may proliferate, and/or may bind to skeletal muscle tissue, differentiate into functional myoblasts, and subsequently develop into functioning myofibers. Transplantation may utilize a dose of cells effective to obtain the desired effect, which may be delivered in an appropriate medium or substrate.

Diseases of interest for treatment with the methods of the invention include heritable and acquired muscle disorders. A number of muscle conditions in which there is muscle wasting such as cachexia, atrophy and sarcopenia, are of interest, e.g. conditions associated with increased age, immobility, drug treatment, cancer, and the like.

In some embodiments, the inherited muscle disorders include, without limitation, muscular dystrophies. For example, Duchenne dystrophy is an X-linked recessive disorder characterized by progressive proximal muscle weakness with destruction and regeneration of muscle fibers and replacement by connective tissue. Duchenne dystrophy is caused by a mutation at the Xp21 locus, which results in the absence of dystrophin, a protein found inside the muscle cell membrane. It affects 1 in 3000 live male births. Symptoms typically start in boys aged 3 to 7 yr. Progression is steady, and limb flexion contractures and scoliosis develop. Firm pseudohypertrophy (fatty and fibrous replacement of certain enlarged muscle groups, notably the calves) develops. Becker muscular dystrophy is a less severe variant, also due to a mutation at the Xp21 locus. Dystrophin is reduced in quantity or in molecular weight. Patients usually remain ambulatory, and most survive into their 30s and 40s.

In some embodiments, muscle disorders include myopathies. In some embodiments, myopathies include, but are not limited to, congenital and metabolic myopathies, including glycogen storage diseases and mitochondrial myopathies. Congenital myopathies are a heterogeneous group of disorders that cause hypotonia in infancy or weakness and delayed motor milestones later in childhood. An autosomal dominant form of nemaline myopathy is linked to chromosome 1 (tropomyosin gene), and a recessive form to chromosome 2. Other forms are caused by mutations in the gene for the ryanodine receptor (the calcium release channel of the sarcoplasmic reticulum) on chromosome 19q. Skeletal abnormalities and dysmorphic features are common. Diagnosis is made by histochemical and electron microscopic examination of a muscle sample to identify specific morphologic changes.

Mitochondrial myopathies range from mild, slowly progressive weakness of the extraocular muscles to severe, fatal infantile myopathies and multisystem encephalomyopathies. Some syndromes have been defined, with some overlap between them. Established syndromes affecting muscle include progressive external ophthalmoplegia, the Kearns-Sayre syndrome (with ophthalmoplegia, pigmentary retinopathy, cardiac conduction defects, cerebellar ataxia, and sensorineural deafness), the MELAS syndrome (mitochondrial encephalomyopathy, lactic acidosis, and stroke-like episodes), the MERFF syndrome (myoclonic epilepsy and ragged red fibers), limb-girdle distribution weakness, and infantile myopathy (benign or severe and fatal). Muscle biopsy specimens stained with modified Gomori's trichrome stain show ragged red fibers due to excessive accumulation of mitochondria. Biochemical defects in substrate transport and utilization, the Krebs cycle, oxidative phosphorylation, or the respiratory chain are detectable. Numerous mitochondrial DNA point mutations and deletions have been described, transmitted in a maternal, nonmendelian inheritance pattern. Mutations in nuclear-encoded mitochondrial enzymes occur.

Glycogen storage diseases of muscle are a group of rare autosomal recessive diseases characterized by abnormal accumulation of glycogen in skeletal muscle due to a specific biochemical defect in carbohydrate metabolism.

These diseases can be mild or severe. In a severe form, acid maltase deficiency (Pompe's disease), in which 1,4-glucosidase is absent, is evident in the first year of life and is fatal by age 2. Glycogen accumulates in the heart, liver, muscles, and nerves. In a less severe form, this deficiency may produce proximal limb weakness and diaphragm involvement causing hypoventilation in adults. Myotonic discharges in paraspinal muscles are commonly seen on electromyogram, but myotonia does not occur clinically. Other enzyme deficiencies cause painful cramps after exercise, followed by myoglobinuria. The diagnosis is supported by an ischemic exercise test without an appropriate rise in serum lactate and is confirmed by demonstrating a specific enzyme abnormality.

Channelopathies are neuromuscular disorders with functional abnormalities due to disturbance of the membrane conduction system, resulting from mutations affecting ion channels. Myotonic disorders are characterized by abnormally slow relaxation after voluntary muscle contraction due to a muscle membrane abnormality.

Myotonic dystrophy (Steinert's disease) is an autosomal dominant multisystem disorder characterized by dystrophic muscle weakness and myotonia. The molecular defect is an expanded trinucleotide (CTG) repeat in the 3' untranslated region of the myotonin-protein kinase gene on chromosome 19q. Symptoms can occur at any age, and the range of clinical severity is broad. Myotonia is prominent in the hand muscles, and ptosis is common even in mild cases. In severe cases, marked peripheral muscular weakness occurs, often with cataracts, premature balding, hatchet facies, cardiac arrhythmias, testicular atrophy, and endocrine abnormalities. Mental retardation is common. Severely affected persons die by their early 50s.

Myotonia congenita (Thomsen's disease) is a rare autosomal dominant myotonia that usually begins in infancy. In several families, the disorder has been linked to a region on chromosome 7 containing a skeletal muscle chloride channel gene. Painless muscle stiffness is most troublesome in the hands, legs, and eyelids and improves with exercise. Weakness is usually minimal. Muscles may become hypertrophied. Diagnosis is usually established by the characteristic physical appearance, by inability to release the handgrip rapidly, and by sustained muscle contraction after direct muscle percussion.

Familial periodic paralysis is a group of rare autosomal dominant disorders characterized by episodes of flaccid paralysis with loss of deep tendon reflexes and failure of muscle to respond to electrical stimulation. The hypokalemic form is due to genetic mutation in the dihydropyridine receptor-associated calcium channel gene on chromosome 1q. The hyperkalemic form is due to mutations in the gene on chromosome 17q that encodes a subunit of the skeletal muscle sodium channel (SCN4A).

Sarcopenia is a term utilized to define the loss of muscle mass and strength that occurs with aging. Sarcopenia is believed to play a major role in the pathogenesis of frailty and functional impairment that occurs with old age. Progressive muscle wasting occurs with aging. The prevalence of clinically significant sarcopenia is estimated to range from 8.8% in young old women to 17.5% in old men. Persons who are obese and sarcopenic (the "fat frail") have worse outcomes than those who are sarcopenic and non-obese. There is a disproportionate atrophy of type IIa muscle fibers with aging. There is also evidence of an age-related decrease in the synthesis rate of myosin heavy chain proteins. Motor units innervating muscle decline with aging, and there is increased irregularity of muscle unit firing. There are indications that cytokines, especially interleukin-1beta, tumor necrosis factor-alpha, and interleukin-6, play a role in the pathogenesis of sarcopenia. Similarly, the decline in anabolic hormones, i.e. testosterone, dehydroepiandrosterone growth hormone, and insulin-like growth factor-I, is also implicated in the sarcopenic process.

Sarcopenia is typically marked by a decrease in the circumference of distinct types of muscle fibers. During sarcopenia, there is a decrease in "type 2" fiber circumference (Type II), with little to no decrease in "type I" fiber circumference (Type I). Diagnosis of sarcopenia may include low muscle mass, >2 standard deviations below that mean measured in young adults (aged 18-39 years in the 3rd NHANES population) of the same sex and ethnic background, and low gait speed (e.g. a walking speed below 0.8 m/s in the 4-m walking test).

Cachexia is wasting of both adipose and skeletal muscle. It occurs in many conditions and is common with many cancers when remission or control fails. Some cancers, especially pancreatic and gastric cancers, cause profound cachexia. Affected patients may lose 10 to 20% of body weight. Men tend to experience worse cachexia with cancer than do women. Neither tumor size nor the extent of metastatic disease predicts the degree of cachexia. Cachexia is associated with reduced response to chemotherapy, poor functional performance, and increased mortality.

The primary cause of cachexia is not anorexia or decreased caloric intake. Rather, this complex metabolic condition involves increased tissue catabolism. Protein synthesis is decreased and degradation increased. Cachexia is mediated by certain cytokines, especially tumor necrosis factor-α, IL-1 b, and IL-6, which are produced by tumor cells and host cells in the tissue mass. The ATP-ubiquitin-protease pathway plays a role as well.

Corticosteroid induced myopathy. Steroid muscle-related involvement is a frequent but often underestimated adverse effect of steroid treatment. Clinical presentation may differentiate two features: the less frequent, represented by acute myopathy, essentially observed in resuscitation, in patients treated with high dosages, and the more frequent feature, insidious, painless, chronic myopathy, characterized by a progressive proximal deficit. Diagnosis is mostly based on the clinic, muscle biopsy should remain exceptional, performed to detect other myopathies, since there are no specific anatomopathological findings. Muscle enzymes are rarely increased, electrophysiological analyses demonstrate unspecific and variable abnormalities. Pathophysiology of steroid-induced myopathy is multifactorial, related to protein metabolism modifications (change of both metabolism and catabolism), cellular transcription, growth factors (IGF-1, myostatine).

Unlike with other drug-induced myopathies, serum CK concentration does not markedly increase with steroid myopathy. EMG is normal or may show low amplitude myopathic motor unit potentials and no signs of neuropathy. Muscle biopsy usually reveals an increased variation in the diameter of fibers and type IIb muscle fiber atrophy without muscle fiber inflammation or necrosis. However, a necrotizing steroid myopathy has also been reported to occur. Proximal muscle weakness of the lower and upper extremities is significantly related to the cumulative dose of steroid. An increase in muscle strength occurring 3-4 weeks after dose reduction usually indicates steroid-induced myopathy. However, chronic myopathy may persist after prolonged treatment with high doses of corticosteroids.

In addition to therapeutic uses, the methods of the invention may be used to increase muscle mass and/or decrease body fat in non-human animals, e.g. livestock, including without limitation, equines, bovines, porcines, ursines, etc., for which increased muscle mass may be desired; pets including canines, felines, etc., animal models for research purposes, and the like. Animals may be treated with the native protein for the species, e.g. bovine ADAMTS1 for increasing muscle mass of bovines; or may be treated with a xenogeneic protein, in which there is sufficient cross-reactivity to generate the desired result.

Obesity.

In general terms obesity denotes excess body fat; the consequences of which depend not only on the absolute amount but also on the distribution of the fat. Complications include cardiovascular disorders, diabetes mellitus, many cancers, cholelithiasis, fatty liver and cirrhosis, osteoarthritis, reproductive disorders in men and women, psychologic disorders, and premature death. Diagnosis is based on body mass index calculated from height and weight, and waist circumference. BP, fasting plasma glucose, and lipid levels should be measured. Treatment includes physical activity, dietary and behavioral modification, and sometimes drugs or surgery.

Heritability of BMI is about 66%. Genetic factors may affect the many signaling molecules and receptors used by parts of the hypothalamus and GI tract to regulate food intake. Rarely, obesity results from abnormal levels of peptides that regulate food intake (eg, leptin) or abnormalities in their receptors (eg, melanocortin-4 receptor). Genetic factors also regulate energy expenditure, including BMR, diet-induced thermogenesis, and nonvoluntary activity-associated thermogenesis. Genetic factors may have a greater effect on the distribution of body fat, particularly abdominal fat, than on the amount of body fat.

Insulin resistance, dyslipidemias, and hypertension (the metabolic syndrome) develop, often leading to diabetes mellitus and coronary artery disease. These complications are more likely in patients with fat that is concentrated abdominally, a high serum triglyceride level, a family history of type 2 diabetes mellitus or premature cardiovascular disease, or a combination of these risk factors.

With aging, body fat increases and is redistributed to the abdomen, and muscle mass is lost, largely because of physical inactivity, but decreased androgens and growth hormone (which are anabolic) and inflammatory cytokines produced in obesity may also play a role.

Methods

The methods of the present invention utilize an ADAMTS1 agonist, as described herein, to enhance myogenesis and regulate adipogenesis and metabolism in vivo. An ADAMTS1 antagonist may be used to decrease myogenesis. The agents also find use in ex vivo cultures for the activation of muscle stem cells/satellite cells. Activation of satellite cells in muscle tissue can result in the production of increased muscle mass in the patient. A useful ADAMTS1 activating agent will usually confer an increase in the number of new fibers by at least 1%, more preferably by at least 20%, and most preferably by at least 50%. An increase in growth of a muscle fiber can be defined as an increase in the diameter where the diameter is defined as the minor axis of ellipsis of the cross section.

A determination of effective dose, and effective combination of agents may be determined empirically, for example using animal models as provided herein. In vitro models are also useful for the assessment of dose and selection of agent. For example, cultures are described herein where the myogenic effect on stem or progenitor cells is evaluated. Such cultures may be used to assay for the effectiveness of agents alone, or in combinations.

Determining a therapeutically or prophylactically effective amount of an ADAMTS1 agonist composition can be done based on animal data using routine computational methods. The effective dose may be measured in terms of increase in muscle mass in the individual over a suitable period of time, e.g. over 2 weeks, 3 weeks, 4 weeks, 5 weeks, 6 weeks, 8 weeks, 12 weeks, or more. In one embodiment, the unit dose of a therapeutically or prophylactically effective amount contains between about 0.01 mg and about 1 g of nucleic acid or protein, as applicable. Typically the administration is performed over a period of time, e.g. semi-daily, daily, semi-weekly, weekly, for a period of days, weeks, months, etc. The methods of the invention find use in the treatment of juveniles, and the dosage may be adjusted accordingly using methods known in the art.

In this invention, administering the instant compositions can be effected or performed using any of the various methods and delivery systems known to those skilled in the art. The administering can be performed, for example, intravenously, orally, via implant, transmucosally, transdermally, intramuscularly, intrathecally, and subcutaneously. The following delivery systems, which employ a number of routinely used pharmaceutical carriers, are only representative of the many embodiments envisioned for administering the instant compositions.

Injectable drug delivery systems include solutions, suspensions, gels, microspheres and polymeric injectables, and can comprise excipients such as solubility-altering agents (e.g., ethanol, propylene glycol and sucrose) and polymers (e.g., polycaprylactones and PLGA's). Implantable systems include rods and discs, and can contain excipients such as PLGA and polycaprylactone. Protein or nucleic acids of the invention can also be administered attached to particles using a gene gun.

Oral delivery systems include tablets and capsules. These can contain excipients such as binders (e.g., hydroxypropylmethylcellulose, polyvinyl pyrilodone, other cellulosic materials and starch), diluents (e.g., lactose and other sugars, starch, dicalcium phosphate and cellulosic materials), disintegrating agents (e.g., starch polymers and cellulosic materials) and lubricating agents (e.g., stearates and talc).

Transmucosal delivery systems include patches, tablets, suppositories, pessaries, gels and creams, and can contain excipients such as solubilizers and enhancers (e.g., propylene glycol, bile salts and amino acids), and other vehicles (e.g., polyethylene glycol, fatty acid esters and derivatives, and hydrophilic polymers such as hydroxypropylmethylcellulose and hyaluronic acid).

Dermal delivery systems include, for example, aqueous and nonaqueous gels, creams, multiple emulsions, microemulsions, liposomes, ointments, aqueous and nonaqueous solutions, lotions, aerosols, hydrocarbon bases and powders, and can contain excipients such as solubilizers, permeation enhancers (e.g., fatty acids, fatty acid esters, fatty alcohols and amino acids), and hydrophilic polymers (e.g., polycarbophil and polyvinylpyrolidone). In one embodiment, the pharmaceutically acceptable carrier is a liposome or a transdermal enhancer.

Solutions, suspensions and powders for reconstitutable delivery systems include vehicles such as suspending agents (e.g., gums, xanthans, cellulosics and sugars), humectants (e.g., sorbitol), solubilizers (e.g., ethanol, water, PEG and propylene glycol), surfactants (e.g., sodium lauryl sulfate, Spans, Tweens, and cetyl pyridine), preservatives and antioxidants (e.g., parabens, vitamins E and C, and ascorbic acid), anti-caking agents, coating agents, and chelating agents (e.g., EDTA).

Formulations may be provided in a unit dosage form, where the term "unit dosage form," refers to physically discrete units suitable as unitary dosages for human subjects, each unit containing a predetermined quantity of active agent in an amount calculated sufficient to produce the desired effect in association with a pharmaceutically acceptable diluent, carrier or vehicle. The specifications for the unit dosage forms of the present invention depend on the particular complex employed and the effect to be achieved, and the pharmacodynamics associated with each complex in the host.

Those of skill will readily appreciate that dose levels can vary as a function of the specific agent, the severity of the symptoms and the susceptibility of the subject to side effects. Some of the agents will be more potent than others. Preferred dosages for a given agent are readily determinable by those of skill in the art by a variety of means. A preferred means is to measure the physiological potency of a given compound.

The subject methods are useful for both prophylactic and therapeutic purposes. Thus, as used herein, the term "treating" is used to refer to both prevention of disease, and treatment of a pre-existing condition. The treatment of ongoing disease, to stabilize or improve the clinical symptoms of the patient, is a particularly important benefit provided by the present invention. Such treatment is desirably performed prior to loss of function in the affected tissues; consequently, the prophylactic therapeutic benefits provided by the invention are also important. Evidence of therapeutic effect may be any diminution in the severity of disease. The therapeutic effect can be measured in terms of clinical outcome or can be determined by immunological or biochemical tests.

For the treatment of disorders in which there is inadequate muscle stem cell activation or there is a deficit of muscle mass due to an injury or disease, an ADAMTS1 agonist is administered at a dose that is effective to cause an increase of myogenesis, but which maintains the overall health of the individual. Treatment regimens may utilize a short-term administration of the active agent; although typically the treatment is administered for prolonged periods, for example as a daily, semi-weekly, weekly, semi-monthly, monthly dose monthly, etc. The size of the dose administered must be determined by a physician and will depend on a number of factors, such as the nature and gravity of the disease, the age and state of health of the patient and the patient's tolerance to the agent itself. For example, a number of conditions relevant to deficits in muscle mass are described above, including cachexia, sarcopenia, myopathies, etc.

For the treatment of disorders in which there is a metabolic dysfunction, e.g. insulin resistance, diabetes, obesity, etc., an ADAMTS1 agonist is administered at a dose that is effective to cause improve the desired target function, e.g. improved insulin sensitivity, decreased adipose tissue, etc., but which maintains the overall health of the individual. Treatment regimens may utilize a short-term administration of the active agent; although typically the treatment is administered for prolonged periods, for example as a daily, semi-weekly, weekly, semi-monthly, monthly dose monthly, etc. The size of the dose administered must be determined by a physician and will depend on a number of factors, such as the nature and gravity of the disease, the age and state of health of the patient and the patient's tolerance to the agent itself.

In Vitro Methods

A population of cells comprising stem cells, e.g. muscle stem cells, mesenchymal stem cell, adipose stem cells or pre-adipocytes, etc. can be cultured in vitro in the presence of an effective dose of an ADAMTS1 agonist or antagonist The cells are maintained in culture for a period of time sufficient to activate muscle stem cells, to induce multipotent stem cells to a muscle fate, or to perform necessary manipulations, genetic or exposure to drugs. The activation of muscle stem cells may be assayed as described in the examples, for example by assaying cells for the expression of genes and proteins specific for muscle cells; detection of fusion into muscle fibers; and the like.

After seeding the culture medium, the culture medium is maintained under conventional conditions for growth of mammalian cells, generally about 37° C. and 5% $CO_2$ in 100% humidified atmosphere. Fresh media may be conveniently replaced, in part, by removing a portion of the media and replacing it with fresh media. Various commercially available systems have been developed for the growth of mammalian cells to provide for removal of adverse metabolic products, replenishment of nutrients, and maintenance of oxygen. By employing these systems, the medium may be maintained as a continuous medium, so that the concentrations of the various ingredients are maintained relatively constant or within a predescribed range. Such systems can provide for enhanced maintenance and growth of the subject cells using the designated media and additives.

Following activation, the cells may be removed from the culture by digestion with enzymes, chelators, etc., as known in the art using time, temperature, concentration and selection of reagents. One of skill in the art can readily perform a simple titration to determine suitable conditions, e.g. using EDTA, elastase; dispase; collagenase; trypsin; blendzyme; and the like.

These cells may find various applications for a wide variety of purposes. The cell populations may be used for screening various additives for their effect on growth and the mature differentiation of the cells. In this manner, compounds which are complementary, agonistic, antagonistic or inactive may be screened, determining the effect of the compound in relationship with one or more of the different cytokines.

The populations may be employed as grafts for transplantation. For example, activated muscle stem cells find use in the regeneration or treatment of muscle; and the like. For therapeutic methods the cells may be used for tissue reconstitution or regeneration in a human patient or other subject in need of such treatment. The cells are administered in a manner that permits them to graft or migrate to the intended tissue site and reconstitute or regenerate the functionally deficient area.

Often, a subject provides cells for the use in the methods and compositions disclosed herein. The subject may be free of a disease condition. In other cases, the subject is suffering from, or at high risk of suffering from, a health condition or even an acute health condition. In certain cases, a subject provides cells for his or her future use, e.g., an autologous therapy, or for the use of another subject who may need treatment or therapy, e.g., an allogeneic therapy.

The activated cells may be administered in any physiologically acceptable excipient, where the cells may find an appropriate site for regeneration and differentiation. The cells may be introduced by injection, catheter, or the like.

The cells may be frozen at liquid nitrogen temperatures and stored for long periods of time, being capable of use on thawing. If frozen, the cells will usually be stored in any suitable medium, for example 10% DMSO, 20% FCS, 70% DMEM medium. Once thawed, the cells may be expanded by use of growth factors and/or feeder cells associated with progenitor cell proliferation and differentiation.

The cells can be supplied in the form of a pharmaceutical composition, comprising an isotonic excipient prepared under sufficiently sterile conditions for human administration. Choice of the cellular excipient and any accompanying elements of the composition will be adapted in accordance with the route and device used for administration. The composition may also comprise or be accompanied with one or more other ingredients that facilitate the engraftment or functional mobilization of the cells. Suitable ingredients include matrix proteins that support or promote adhesion of the cells.

The dosage of the therapeutic formulation will vary widely, depending upon the nature of the condition, the frequency of administration, the manner of administration, the clearance of the agent from the host, and the like. The initial dose can be larger, followed by smaller maintenance doses. The dose can be administered as infrequently as weekly or biweekly, or more often fractionated into smaller doses and administered daily, semi-weekly, or otherwise as needed to maintain an effective dosage level.

Screening

In another aspect of the invention, a method is provided for in vitro screening for agents for their effect on cells expanded using the culture conditions of the present invention. For example, stem cells cultured by the methods described herein are exposed to candidate agents. Agents of interest include, but are not limited to, pharmaceutical and genetic agents, e.g. antisense, expressible coding sequences, RNAi, and the like, where the genetic agents may correspond to candidate muscle differentiation or activation agents, and the like. In some embodiments, the effect on the cell phenotype is determined. Agents active on activated muscle stem cells are detected by changes in growth of the cultured cells, e.g. in their ability to participate in in vivo regeneration; expression of markers indicative of stem cells; and the like.

Manipulations may include, but are not limited to, genetic modification; epigenetic modification; fusion with another cell or cells; adaptation of the cells to a chemical stimulus; dedifferentiation; transdifferentiation; change in expression level of one or more genes; change in state of signaling pathways or metabolic pathways; extension of telomeres; freezing, storage, or thawing; rejuvenation of one or more cellular functions; rejuvenation of one or more cellular structures or components; repair or replacement of DNA; repair or replacement of mitochondria; repair or replacement of cellular components; removal of waste products; covalent modification of cellular proteins, lipids, or carbohydrates; exposure to a drug; exposure to a cell; exposure to a polypeptide; expanding the number of cells.

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

All publications and patent applications cited in this specification are herein incorporated by reference as if each individual publication or patent application were specifically and individually indicated to be incorporated by reference.

The present invention has been described in terms of particular embodiments found or proposed by the present inventor to comprise preferred modes for the practice of the invention. It will be appreciated by those of skill in the art that, in light of the present disclosure, numerous modifications and changes can be made in the particular embodiments exemplified without departing from the intended scope of the invention. For example, due to codon redundancy, changes can be made in the underlying DNA sequence without affecting the protein sequence. Moreover, due to biological functional equivalency considerations, changes can be made in protein structure without affecting the biological action in kind or amount. All such modifications are intended to be included within the scope of the appended claims.

EXPERIMENTAL

Example 1

In order to identify pathways that regulate muscle differentiation, we performed a time-course (48 hour) microarray study following exposure of FACS purified primary mouse MuSCs to glucocorticoids. MuSCs are defined as cells isolated from primary muscle tissue with a FACS profile of CD34+α7integrin+ and CD45−, CD11 b−, CD31−, Sca1−. This work revealed that expression of Adamts1, a secreted protein, was highly repressed by glucocorticoids. Adamts1 is an especially appealing 'hit' because the extracellular location makes it a particular accessible or 'drugable' target for developing therapies.

Figure 2C:
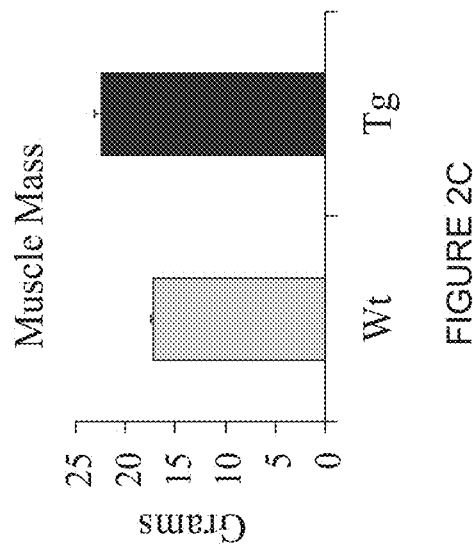
FIGS. 2A-2C. C2C12 cells were induced to mature into myoblasts by overexpression of ADAMTS1, or by addition of purified recombinant ADAMTS1 protein (rADAM) into the culture media at 10-20 ng/ml dissolved in media. Analysis was performed after 4 days of culture.
Figure 2A:
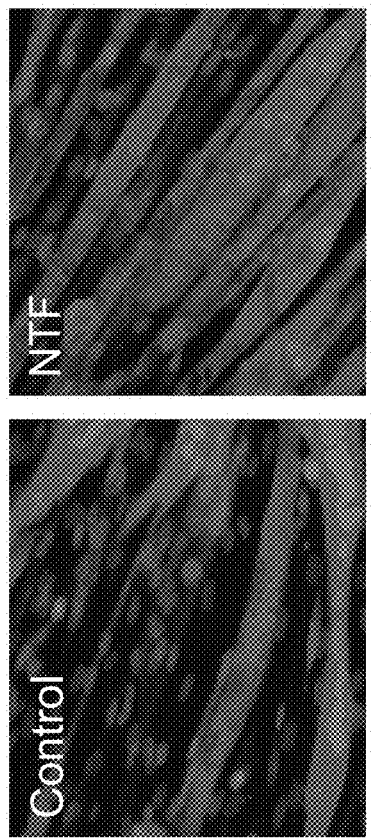
Figure 2B:
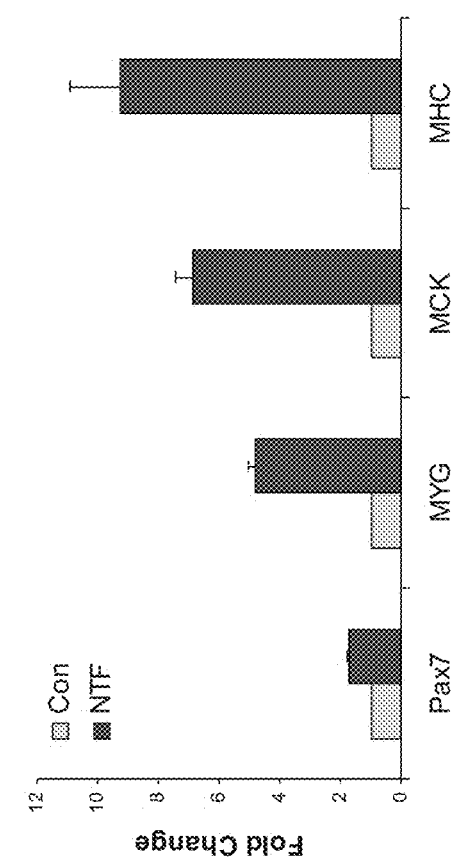

The repression of Adamts1 expression by glucocorticoids is robust using quantitative real-time RT-qPCR. We then overexpressed Adamts1, by nucleofecting (Neon) a pEF5-Adamts1 expression plasmid or empty pEF vector control, into MuSCs and monitored for evidence of muscle formation (myogenesis) after 5 days. We found that a 8-fold overexpression of Adamts1 in MuSCs resulted in a significant induction of multiple muscle specific markers (FIG. 1). To confirm that myogenesis was induced by an extracellular signal (rather than intracellular), we generated recombinant Adamts1 (rADAM) by overexpressing GST-tagged ADAMTS1 in *Escherichia coli* and purifying the protein using glutathione-agarose beads. We then exposed purified MuSCs to either 15 nM rADAM or GST control. As demonstrated by both immunohistochemistry and RT-qPCR of muscle specific factors, ADAMTS1 enhanced myogenesis compared to the GST treated control (FIG. 2).

To test the in vivo relevance of these finding, for example to assess if Adamts1 leads to the induction of mature myocytes and increased muscle mass, we generated transgenic mice that overexpress Adamts1. We wanted to confirm that the impact on muscle was the result of an extracellular signal in vivo. Therefore, we used an aP2 promoter/enhancer element to drive transgene expression as we, and others, have shown that this promoter is active in adipose tissue but is not active in muscle tissue. In other words, we harnessed adipose tissue to secrete ADAMTS1 and expose the MuSCs to ADMATS1 overexpression (FIG. 9A). 3 founder lines were generated in a pure C57Bl/6 background, which overexpress approximately 4, 15 and 20 fold excess Adamts1 respectively, as detected by RT-qPCR on adipose tissue.

It was confirmed that the transgenic mice have stable production and secretion of ADAMTS1 protein by detecting ADAMTS1 in the circulation of the mice by western blotting, using the specific HA tag that was fused to the transgene (FIG. 9B). The line with 15-fold excess Adamts1 was used for most experiments, but the results were confirmed in at least one of the other lines. Monitoring total body weight over time, it was found that Adamts1 mice have similar body weights to littermate controls at weaning, but by 3 months of age they are heavier and this trend continued over the 6 months of monitoring (FIG. 9C). FIG. 9D, increased wet weights of transgenic tibialis anterior (TA) muscle and quadriceps skeletal muscles are in 3 month old ADAMTS1 transgenic mice compared to control animals. Shown in FIG. 9E, hematoxylin and eosin (H&E) staining shows larger myofibers in 3 month old transgenic mice, and a quantitation of myofiber diameter reveals increased fiber size in 3 month old transgenic mice (FIG. 9E. Note: At least 3 pair of animals are used in the experiments. Wild type littermates were used as controls in all experiments.

Figure 3A:
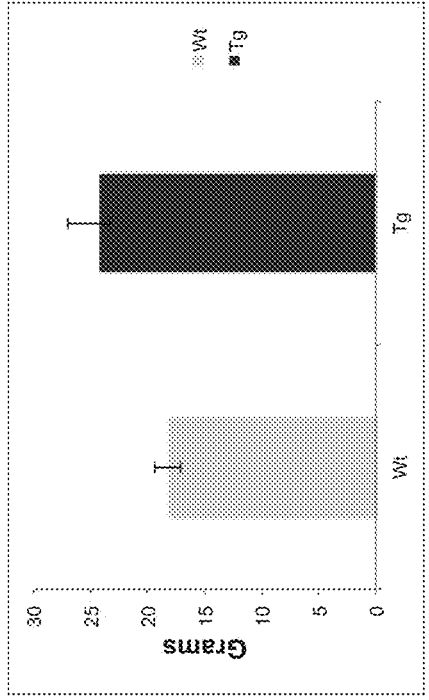
FIG. 3A-3B. Increase of muscle mass in ADAMTS1 transgenic, shown by weight. Duration of time Adamts1 transgenic mice (Tg) were able to continue on a treadmill compared to wild-type (Wt) littermate controls shows enhanced endurance in the Tg animals. Adam mice are resistant to the loss of endurance caused by aging. N=4 mice per cohort. Mice were placed on a treadmill at 1 month and 3 months of age and the time to falling off was compared across the time points. Wild-type mice stay on the treadmill for a shorter time after aging while Adam mice actually have improved endurance compared to the earlier time point. P<0.0035.

To assess the impact of overexpressing Adamts1 in vivo specifically on muscle tissue, body composition surveys were performed on 3 month-old transgenic animals compared to wild-type littermate controls, using DEXA scanning. These studies demonstrate that the transgenic mice have 23% (+/−3%) more muscle mass than wild type littermate controls. Gross dissection and histologic examinations of the muscle tissue directly confirmed the imaging results and revealed that the myofiber size is increased in Adamts1 animals compared to littermate controls (FIGS. 2, 3A). These important results indicate that overexpression of Adamts1 increases muscle mass in vivo.

Figure 3B:
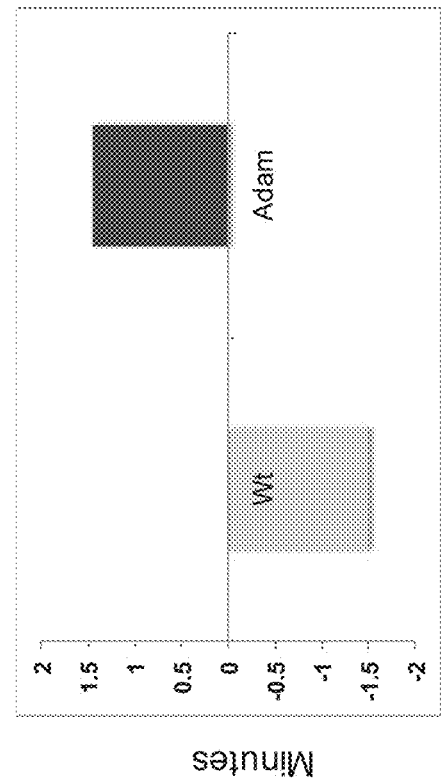
Figure 4:
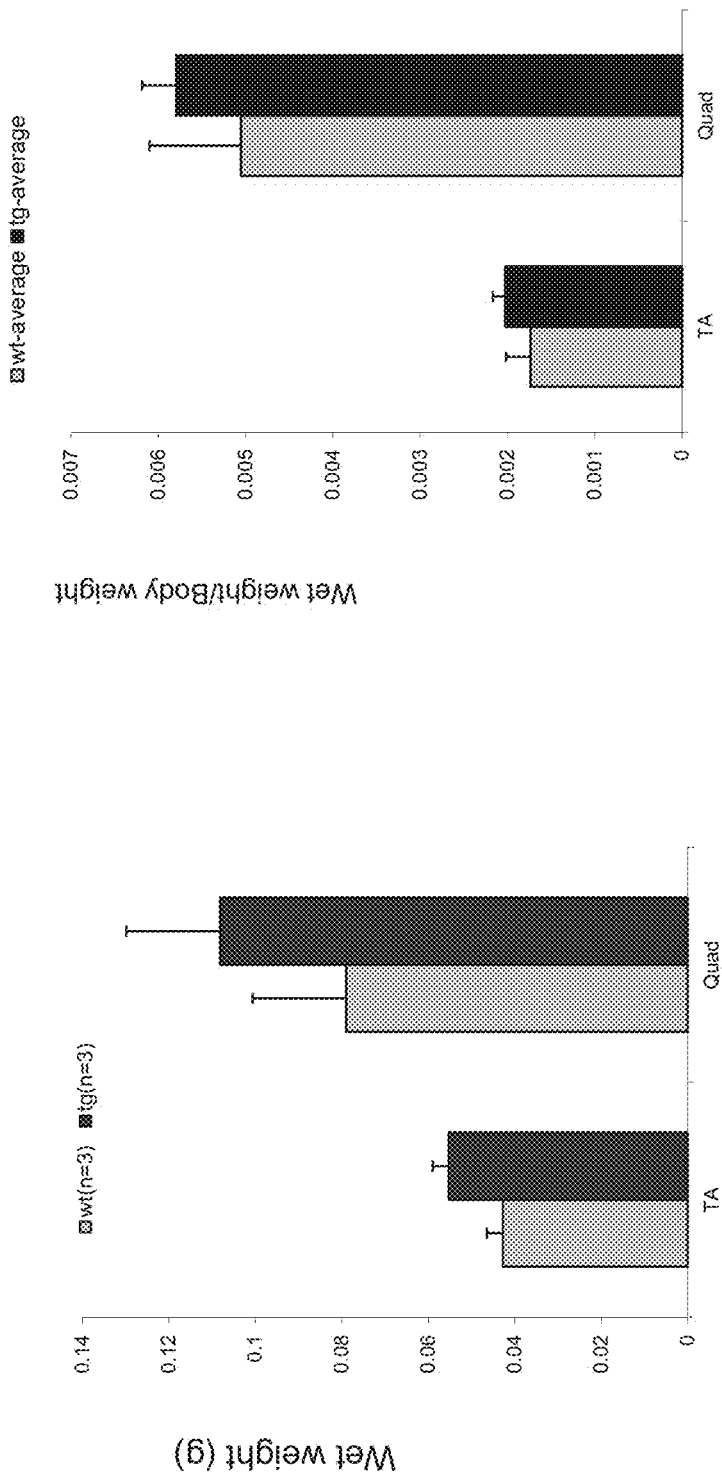
FIG. 4. Total body weight and absolute muscle wt of wild-type and transgenic mice.
Figure 5:
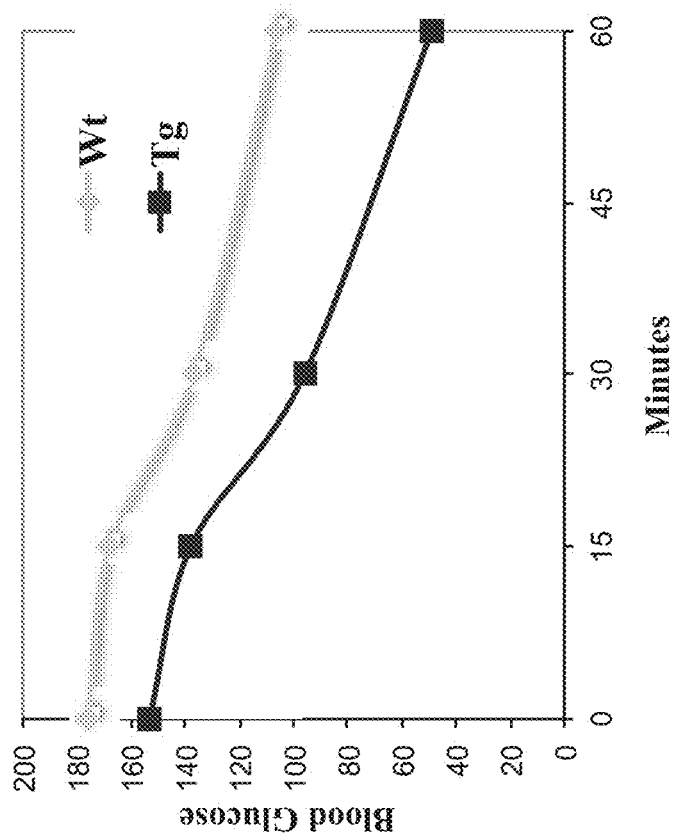
FIG. 5. ADAMTS1 transgenic animals have improved glucose tolerance/insulin sensitivity relative to a control mouse. Insulin was administered at 0.75 U/kg at time 0, and blood glucose was measured.
Figure 6:
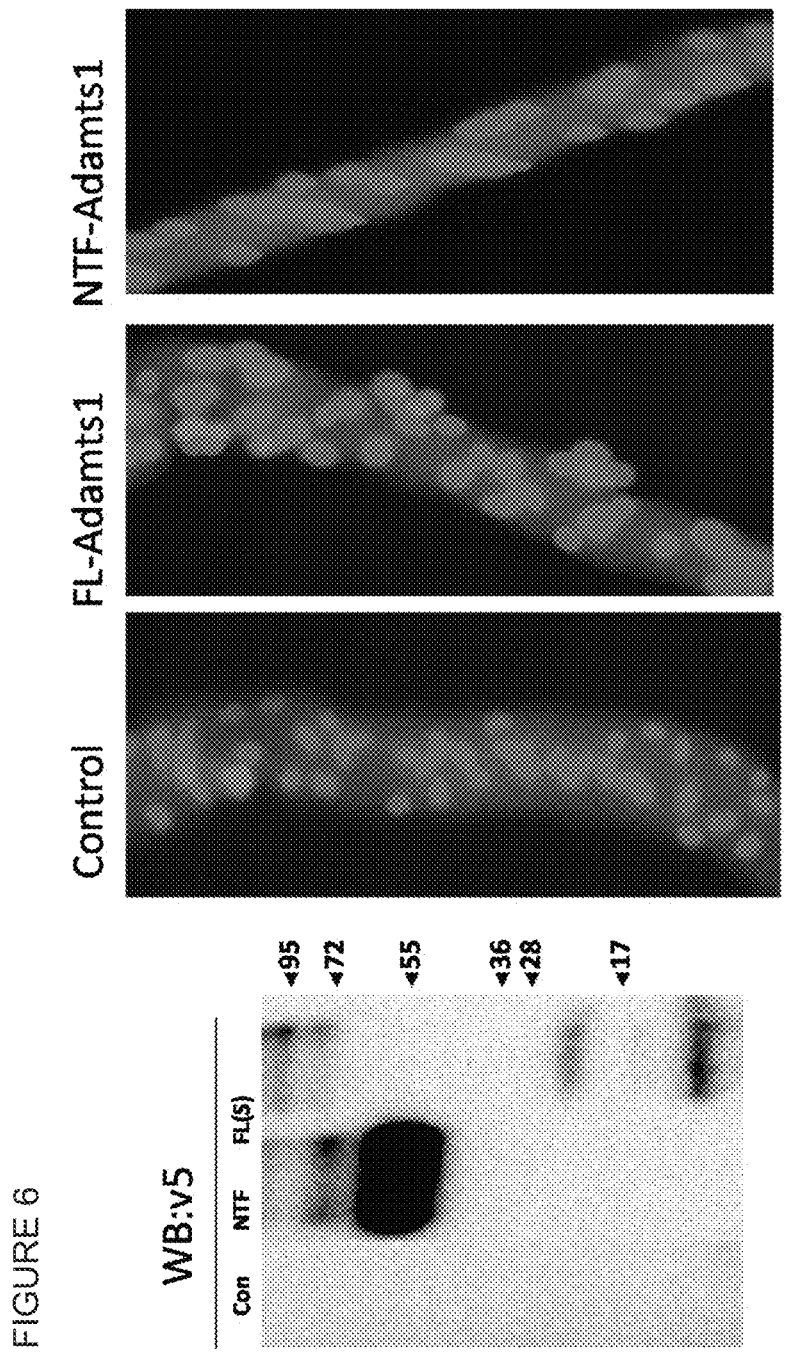
FIG. 6. TA skeletal muscle myofibers were isolated from a 3 week old male mouse and suspended in media with 20% FBS. The myofibers were treated with recombinant ADAMTS1 protein, and cultured for 3 days with a 50% change in medium and protein every day. After day 4 the myofibers were stained with 1:20 Pax7. The data show that Adamts1 promotes satellite cell proliferation.
Figure 7:
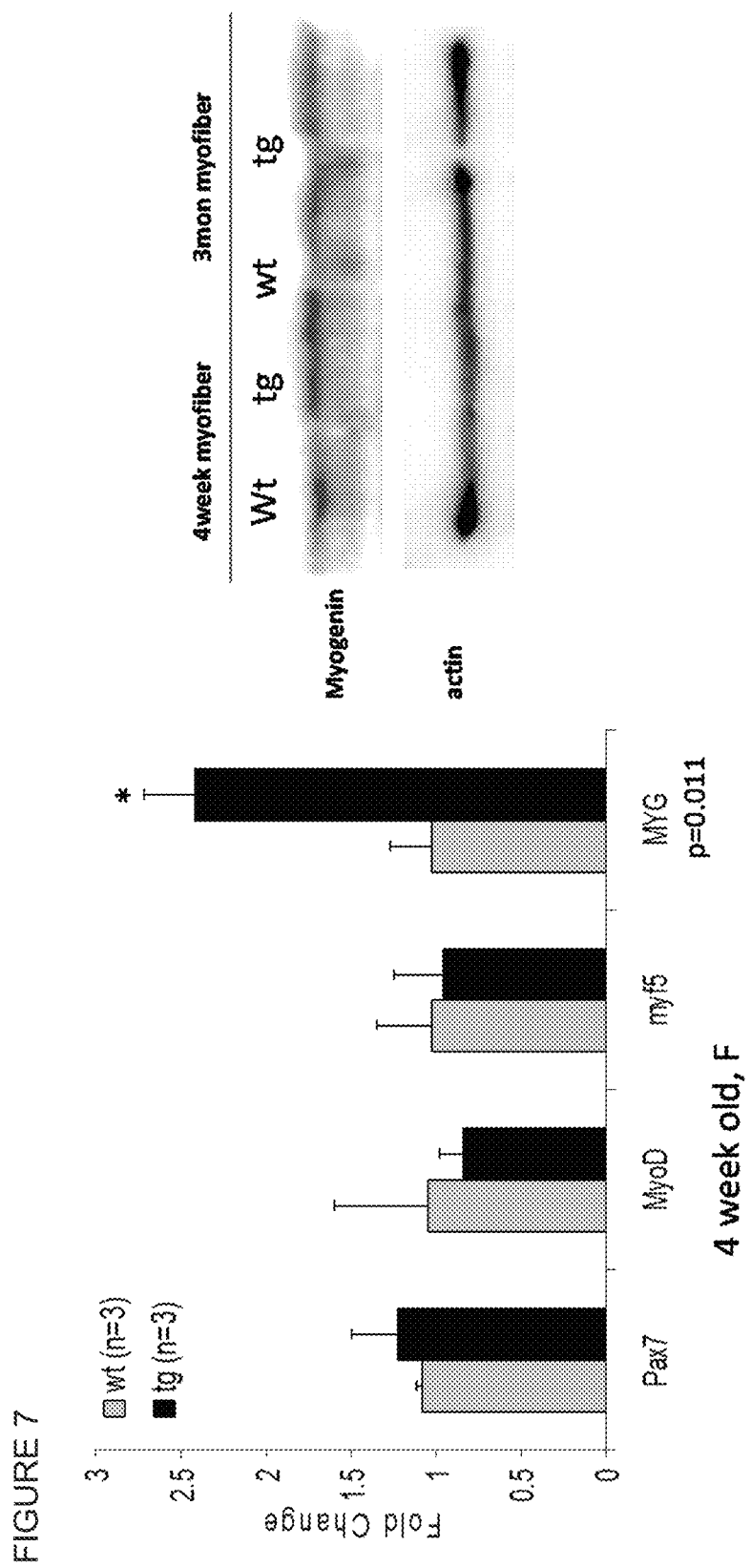
FIG. 7. Primary satellite cells from ADAMTS1 transgenic animals have increased myogenin in vivo.
Figure 8:
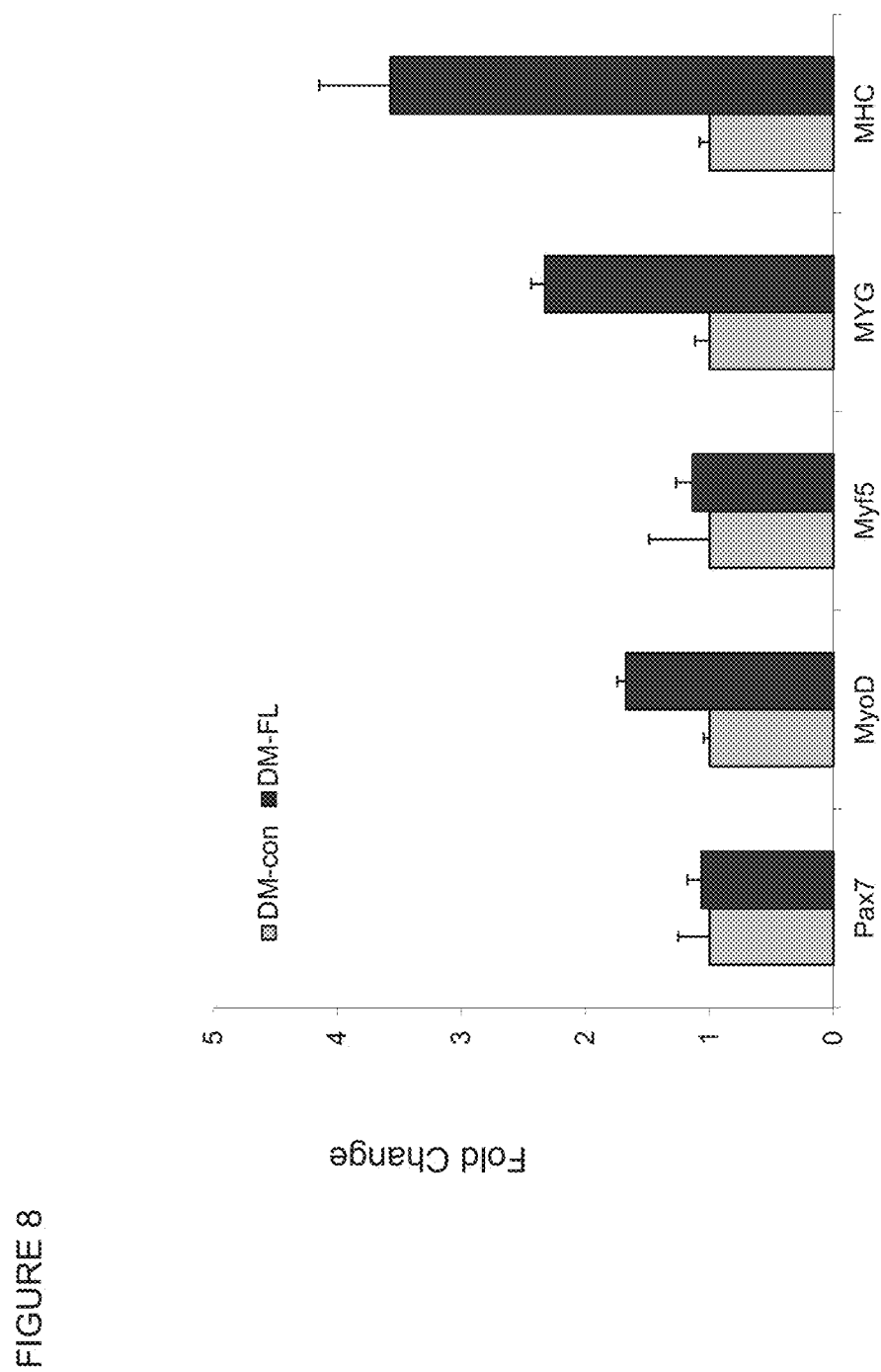
FIG. 8. Effect of ex vivo treatment of satellite cells with recombinant Adamts1.

A study measuring endurance in 3 transgenic compared 3 Wt littermate mice was performed and found that transgenic mice are able to continue on a treadmill test longer than control animals (FIG. 3B). These data and the insulin tolerance test reassure us that the increased muscle mass is functional and physiologically relevant. The increased muscle mass in Adamts1 transgenic mice is consistent with a mechanism of action that acts via an in vivo The effectiveness of ADAMTS1 in vivo and ex vivo was assessed for promotion of satellite cell activation, leading to increased proliferation and differentiation. Protein was produced by recombinant expression in CHO cells, and isolated by a his-tag added to the protein coding sequence. As shown in FIG. 10B, isolated myofibers were treated with 15 nM recombinant ADAMTS1 protein for 3 days in conventional growth medium, then satellite cells were stained for expression of pax7 (paired box protein) shown as the red spots against an overall staining pattern with DAPI (which stains all nuclei). Pax7 is a transcription factor that plays a role in myogenesis through regulation of muscle precursor cell proliferation. It can be seen that there is increased proliferation of muscle cell precursors in the presence of ADAMTS1. Also shown in FIG. 10C, the number of (Pax7)-positive satellite cells were significantly increased in the myofibers treated with recombinant Adamts1. ***p<0.001.

In vivo, 5 week old mice were injected with 5-ethynyl-2-deoxyuridine (EDU) for 14 days, then the EDU-positive satellite cells per myofiber were counted. EDU allows rapid visualization of proliferating cells by incorporation in DNA. EDU+ cells are significantly increased in the myofibers isolated from Adamts1 transgenic mice (as described above), shown in FIG. 10D.

Recombinant Adamts1 promotes satellite cell differentiation in vitro and myogenesis. Muscle satellite cells were purified by flow cytometry for expression of Sca1 and Vcam. The purified cells were cultured in vitro and treated with 15 nM recombinant Adamts1 and control proteins isolated from CHO supernatant, as shown in FIG. 10E. The panel shows "DM-FLs" (ADAMTS1, full length) and "DM-CON" (control). Expression of myogenic markers was assessed by quantitative PCR. It can be seen that the cells exposed to ADAMTS1 had a greater increase in myogenesis markers, relative to the control-treated cells.

Satellite cells were also sorted by FACS from wild-type and Adamts1 transgenic mice that had been administered EDU for 14 days. The satellite cells were plated and immediately assayed for the incorporation of EDU and the expression of myoD, tested by qRT-PCR. Satellite cells from Adamts1 transgenic mice have increased number of EDU incorporation, and are progressing along toward to myogenesis as evidenced by the increased expression of MyoD.

Shown in FIG. 10F, cells were isolated from the tibialis muscle of animals that were injected with Edu, that marks (detected in green) proliferating cells (i.e. muscle progenitors) in vivo and then ex vivo stained for MyoD (marked in Red) to determine if the muscle progenitors are activated. Cells that are yellow are both Edu and MyoD positive (yellow). The data show that Adamts1 mice have more activated muscle progenitors in vivo.

Incorporation of satellite cells into adjacent myofibers. The transgenic ADAMTS1 animals and control wild-type mice at 4 months of age were treated daily with EDU for 14 days, and the tibialis anterior muscle was dissected out, cross-sectioned and stained with 4',6-diamidino-2-phenylindole (DAPI), and with an antibody specific for dystrophin. Shown in FIG. 11A, the EDU+ cells are highlighted by white arrows and are more prevalent in the transgenic animals. Higher power magnification (FIG. 11B) shows that EDU positive cells are myonuclei located beneath the myofiber membrane as delineated by dystrophin staining. Quantification of EDU-positive myoblast cells in FIG. 11C shows a significant increase in the proliferating, EDU positive cells in the transgenic as compared to control mice.

Figure 12B:
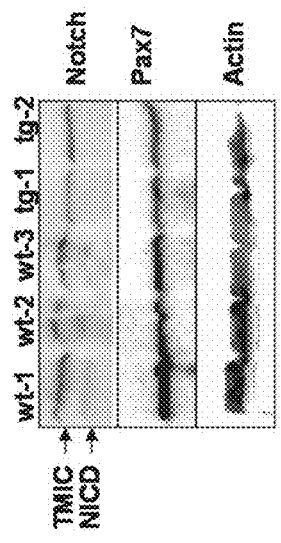
FIG. 12A-12D. Adamts1 represses Notch signaling pathway.
Figure 12A:
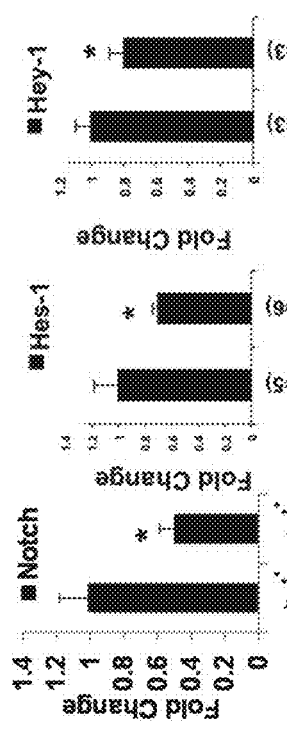

Adamts1 represses Notch signaling pathway. Shown in FIG. 12A, the transgenic mice overexpressing ADAMTS1 repressed Notch pathway expression in vivo as determined by expression of Notch1 and downstream targets of Hes1, Hey1. Expression was measured by real time RT-quantitative PRC.

Primary myoblasts were isolated by dissection from wild-type and transgenic mice at 4 months of age, and a cell lysate run on a western blot and stained with antibodies specific for Notch, Pax7 and actin. Anti-Notch antibody was purchased from Fisher, used at 1:1000 dilution from 0.5 mg/ML stock. anti-Pax7 Ab was obtained from Developmental Studies Hybridoma Bank. Hybridoma supernatant was used to probe blot. The Notch active form (NICD) was undetectable in the Adamts1 mice on the western blot, in which actin serves as the loading control, while the Notch transmembrane domain (TMIC) is unchanged. The TMIC form of Notch does not detectably change but the processed (activated form) form called NICD is markedly reduced which indicates that there is a decrease in Notch activation. These data show that Adamts1 reduces Notch1 cleavage to the active form of the protein. Pax7 expression is also decreased in transgenic mice compared to WT controls.

Induction of Adamts1 was coordinated with repressed Notch pathway after injury in wild type animals. Primary muscle tissue was injured with injections of 1.2% $BaCl_2$.

Figure 12C:
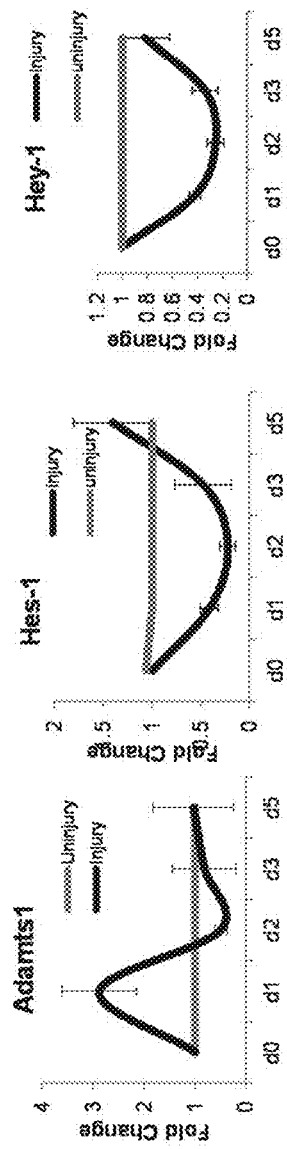
Figure 12D:
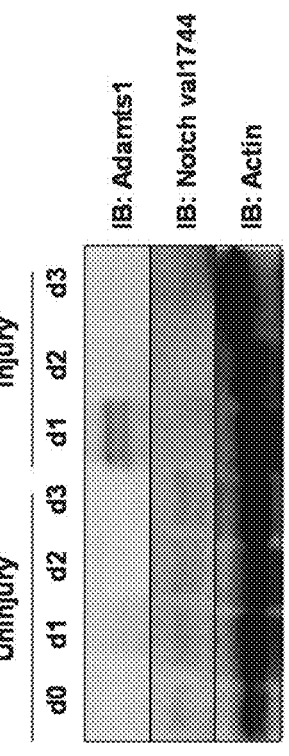

The effect on Notch signaling pathway determine by qRT-PCR (FIG. 12C) of ADAMTS1, the downstream Notch targets Hes-1 and Hey-1. The change in ADAMTS1 expression can also be seen by western blot (FIG. 12D). These data show that when ADAMTS1 goes up physiologically in response to injury, activated Notch goes down. The Val1744 antibody recognizes the cleaved/activated form of Notch.

FIG. 13. Adamts1 modulates processing of Notch1 and its ligand, DLL1 and disrupts binding between Notch1 and DLL1. a, Adamts1 binds to Notch1 by coimmunoprecipitation in 293T cells. Proteins were overexpressed by transfecting the cells with expression plasmids. IP=immunoprecipitated IB+ Immunoblotted. The Adam protein has a V5 tag on it, so Notch was IP's but Adam was detected (by V5 IB) showing that they interact.

Figure 13B:
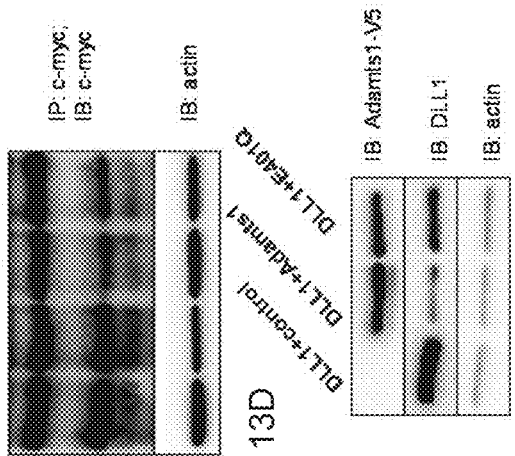
FIG. 13A-13E. Adamts1 modulates processing of Notch1 and its ligand, DLL1 and disrupts binding between Notch1 and DLL1.

Shown in FIG. 13B, Notch 1, DLL1b, and ADAMTS1 or control were provided as shown in the figure. The designated expression constructs were transfected into cells, as noted on the gel. Notch is activated upon ligand-induced conformation change of the Notch negative regulatory region (NRR) unmasking a key proteolytic site (S2) and facilitating downstream events. This experiment is showing that Adamts1 binds to the Notch ligand Dll1. Adamts1 is tagged with V5, DLL is being recognized with an anti-DLL1 antibody.

Figure 13D:
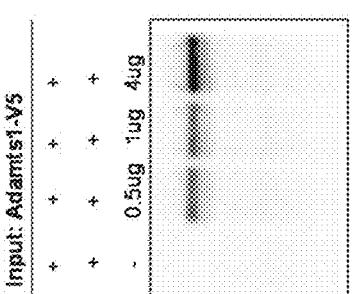
Figure 13A:
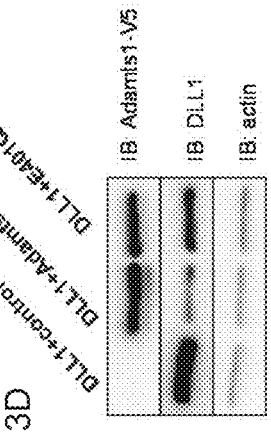
Figure 13A:
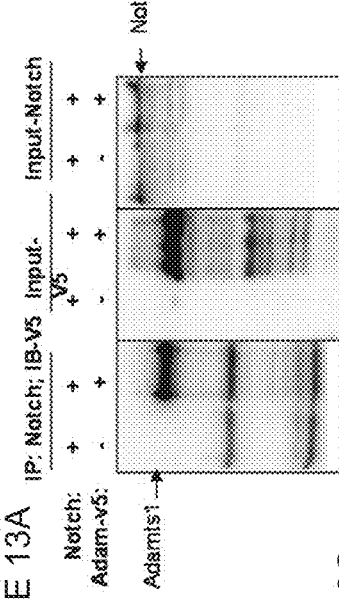
Figure 13C:
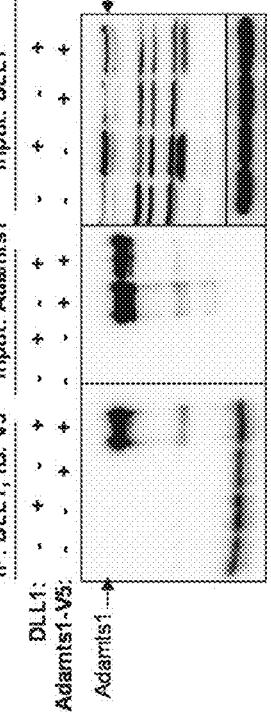

Shown in FIG. 13C, ADAMTS1 also binds to the Notch ligand DLL1 in 293T cells, which is independent of the metalloproteinase activity (shown in FIG. 13D). The V5 designates that Adamts1 is V5 tagged. The input is the cell lysate before IP it is shown to demonstrate that the proteins are successfully expressed and the + means that the cells were transfected with that expression contruct and the – means that they were not. we include lanes without the protein there (–) as controls that demonstrate the specificity of the interaction. The E401Q is mutation in ADAMTS1 that abrogates protease activity, showing that this activity of ADAMTS1 is metalloprotease independent.

Figure 13E:
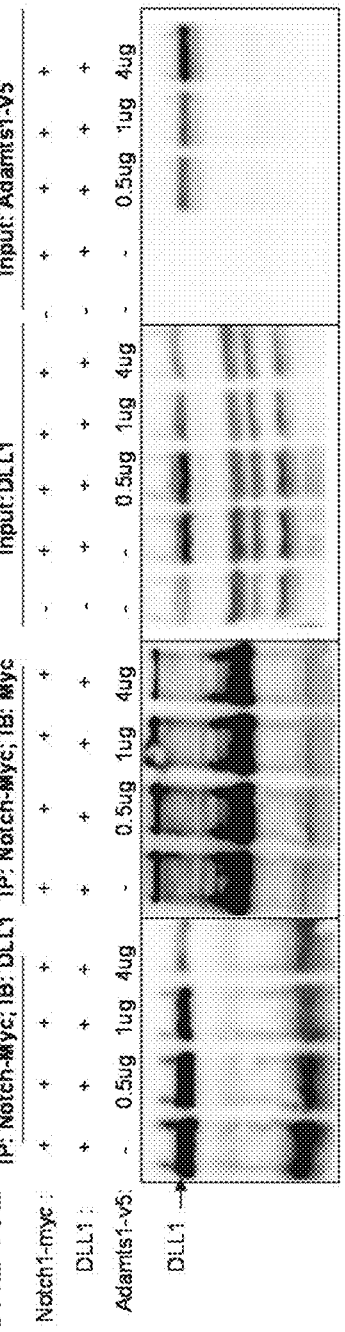

Shown in FIG. 13E, Adamts1 interferes with the binding of Notch1 to its ligand DLL1 in a dose dependent manner, as shown by the immunoprecipitation of Notch and loss of DLL1 staining with higher concentrations of ADAMTS1.

FIG. 14. Mapping of Adamts1 binding to Notch1 and DLL1. a, Diagram of serial deletion of Adamts1 proteins. b, Adamts1 interacts with Notch1. c, Adamts1 interacts with DLL1. The interaction domain is proximal to the metalloprotease domain (and may include it) but metalloprotease activity is not required for the interaction, or for ADAMTS1 to block the Notch-Notch ligand interaction.

Shown in FIG. 15, the promotion of myogenesis activity by Adamts1 is captured in a fragment on the N-terminal side. The C-terminal fragment (CTF, or TSP), which is naturally generated, serves as an inhibitor of myogenesis. In FIG. 15A, C2C12 cells were grown in the presence of recombinant C-terminal fragment (rTSP) into the culture media at 10-20 ng/ml dissolved in media, or a negative control (GST). Analysis was performed after 4 days of culture. A) Immunohistochemistry of myosin heavy chain (MHC) (with DAPI staining to show nuclei) in induced C2C12 cells supports that CTF treatment decreases myogenesis relative to GST control treatment. FIG. 15B shows the purification from supernatant from CHO cells overexpressing just the CTF. FIG. 15C shows a fusion index (the percent of myogenic nuclei present in the myofiber) of the same cells, and a positive control that was treated with the active, recombinant N-terminal fragment of ADAMTS1. FIG. 15D shows the expression by quantitative PCR of muscle associated markers for the CTF (TSP) treated cells, where the fold change is relative to the GST control cells. FIG. 15D shows a Western blot of the same cells, assessed for expression of p21, which is decreased in the CTF (TSP) treated cells. These data demonstrate that the C-terminal fragment of ADAMTS1 inhibits myogenesis.

Shown in FIG. 16, ADAMTS1 inhibits adipogenesis. Progenitor cells from the transgenic animal described above have increased myohenesis and decreased adipogenesis, as shown in FIG. 16A. There is a decreased expression of AP2 and PPARγ as shown in FIG. 16B, with increased expression of muscle specific markers, shown in FIG. 16C.

What is claimed is:

1. A method of enhancing myogenesis, the method comprising:
   contacting a population of human muscle satellite cells in vivo in an individual suffering from a myopathy with an effective dose of a polypeptide consisting of SEQ ID NO:4, wherein the dose is effective to increase muscle mass or to reduce loss of muscle mass in the individual.

2. A method of enhancing myogenesis, the method comprising:
   administering to an individual suffering from a myopathy an effective dose of a purified active fragment of human ADAMTS1 protein comprising SEQ ID NO:1, residues 258-463; thereby contacting a population of human muscle satellite cells, wherein the dose is effective to increase muscle mass or to reduce loss of muscle mass in the individual.

3. The method of claim 2, wherein the active fragment of human ADAMTS1 protein comprises the polypeptide of SEQ ID NO:4.

4. The method of claim 3, wherein the active fragment lacks ADAMTS1 C-terminal portion from residues 725-967.

5. The method of claim 2, wherein the active fragment is administered by intramuscular injection.

6. The method of claim 5, wherein the active fragment consists of the polypeptide of SEQ ID NO:4.

7. The method of claim 1 or claim 2, wherein the myopathy consists of sarcopenia.

* * * * *